United States Patent
Lu et al.

(10) Patent No.: US 9,701,981 B2
(45) Date of Patent: Jul. 11, 2017

(54) NUCLEOSOME-EXCLUDING SEQUENCES (NES) AS A DNA SPACER IN VECTORS RESULTS IN PROLONGED TRANSGENE EXPRESSION IN EUKARYOTIC CELLS

(71) Applicant: The Board of Trustees of the Leland Stanford Junior University, Palo Alto, CA (US)

(72) Inventors: Jiamiao Lu, Mountain View, CA (US); Mark A. Kay, Los Altos, CA (US); Andrew Fire, Stanford, CA (US); Lia E. Gracey Maniar, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 14/205,008

(22) Filed: Mar. 11, 2014

(65) Prior Publication Data
US 2014/0273225 A1    Sep. 18, 2014

Related U.S. Application Data

(60) Provisional application No. 61/798,326, filed on Mar. 15, 2013.

(51) Int. Cl.
| | |
|---|---|
| *C12N 15/67* | (2006.01) |
| *C12N 15/85* | (2006.01) |
| *C12N 15/09* | (2006.01) |
| *C12N 15/63* | (2006.01) |
| *C12P 21/02* | (2006.01) |

(52) U.S. Cl.
CPC .................................. *C12N 15/85* (2013.01)

(58) Field of Classification Search
None
See application file for complete search history.

(56) References Cited

U.S. PATENT DOCUMENTS

2009/0311786 A1* 12/2009 Fire et al. ...................... 435/455

OTHER PUBLICATIONS

Prelle et al., "Establishment of Pluripostent Cell Lines from Vertebrate Species—Present Status and Future Prosepects" 165 Cells Tissues Organs 220-236 (1999).*
Niemann, "Transgenic farm animals get off the ground" 7 Transgenic Research 73-75 (1998).*
Sigmund, "Viewpoint: Are Studies in Genetically Altered Mice Out of Control?" 20 Arteriosclerosis, Thrombosis, and Vascular Biology 1425-1429 (2000).*
Smith, "Gene transfer in higher animals: theoretical considerations and key concepts" 99 Journal of Biotechnology 1-22 (2002).*
Montoliu, "Gene Transfer Strategies in Animal Transgenesis" 4(1) Cloning and Stem Cells 39-46 (2002).*
Ristevski, "Making Better Transgenic Models" 29 Molecular Biotechnology 153-163 (2005).*
Cameron, "Recent Advances in Transgenic Technology" 7 Molecular Biotechnology 253-265 (1997).*
Bao; et al. "Nucleosome core particles containing a poly(dA.dT) sequence element exhibit a locally distorted DNA structure", J Mol Biol (Aug. 2006), 361(4):617-624.
Belch; et al. "Weakly Positioned Nucleosomes Enhance the Transcriptional Competency of Chromatin", PLos One (2010), 5(9): e12984.
Blow; et al. "Chromosome replication in cell-free systems from Xenopus eggs", Philos Trans R Soc Lond B Biol Sci (Dec. 1987), 317(1187):483-494.
Chen; et al. "Minicircle DNA vectors devoid of bacterial DNA result in persistent and high-level transgene expression in vivo", Mol Ther (Sep. 2003), 8(3):495-500.
Chen; et al. "Silencing of episomal transgene expression by plasmid bacterial DNA elements in vivo", Gene Ther (May 2004), 11(10):856-864.
Claeys Bouuaert; et al. "A simple topological filter in a eukaryotic transposon as a mechanism to suppress genome instability", Mol Cell Biol (Jan. 2011), 31(2):317-327.
Datta; et al. "Nucleosomal occupancy and CGG repeat expansion: a comparative analysis of triplet repeat region from mouse and human fragile X mental retardation gene 1", Chromosome Res (May 2011), 19(4):445-455.
Ehrhardt; et al. "A new adenoviral helper-dependent vector results in long-term therapeutic levels of human coagulation factor IX at low doses in vivo", Blood (Jun. 2002), 99(11):3923-3930.
Ganapathi; et al. "A whole genome analysis of 5' regulatory regions of human genes for putative cis-acting modulators of nucleosome positioning", Gene (Apr. 2007), 391(1-2):242-251.
Hino; et al. "Sea urchin arylsulfatase insulator exerts its anti-silencing effect without interacting with the nuclear matrix", J Mol Biol (Mar. 2006), 357(1):18-27.
Lu; et al. "The Extragenic Spacer Length Between the 5' and 3' Ends of the Transgene Expression Cassette Affects Transgene Silencing From Plasmid-based Vectors", Mol Ther (Nov. 2012), 20(11): 2111-2119.
Lyer; et al. "Mechanism of differential utilization of the his3 TR and TC TATA elements", Mol Cell Biol (Dec. 1995), 15 (12)1059-7066.
Montecino; et al. "Nucleosome organization and targeting of SWI/SNF chromatin-remodeling complexes: contributions of the DNA sequence", Biochem Cell Biol (Aug. 2007), 85(4):419-425.
Nakai; et al. "Extrachromosomal recombinant adeno-associated virus vector genomes are primarily responsible for stable liver transduction in vivo", J Virol (Aug. 2001), 75(15):6969-6976.
Segal; et al. "From DNA sequence to transcriptional behaviour: a quantitative approach", Nat Rev Genet (Jul. 2009), 10(7):443-456.
Segal; et al. "Poly(dA:dT) tracts: major determinants of nucleosome organization", Curr Opin Struct Biol (Feb. 2009),19(1):65-71.

(Continued)

*Primary Examiner* — Nancy J Leith
(74) *Attorney, Agent, or Firm* — Kyle A. Gurley; Bozicevic, Field & Francis LLP

(57) ABSTRACT

The silencing effect of a spacer sequence, for example a bacterial backbone sequence in a plasmid or other episomal vector, on transgene expression is reversed by engineering of the spacer to include nucleosome exclusion sequences.

18 Claims, 15 Drawing Sheets

(56) References Cited

OTHER PUBLICATIONS

Segal; et al. "What controls nucleosome positions?" Trends Genet (Aug. 2009), 25(8):335-343.
Tillo; et al. "High nucleosome occupancy is encoded at human regulatory sequences", PLoS One (Feb. 2010), 5(2): e9129.
Waterborg; et al. "Common features of analogous replacement histone H3 genes in animals and plants", J Mol Evol (Sep. 1996), 43(3):194-206.
Xu; et al. "Genome-wide identification and characterization of replication origins by deep sequencing", Genome Biol (Apr. 2012), 13(4):R27.
Yasuda; et al. "Nucleosomal structure of undamaged DNA regions suppresses the non-specific DNA binding of the XPC complex", DNA Repair (Amst) (Mar. 2005), 4(3):389-395.
Yu; et al. "Mechanism of the Long Range Anti-Silencing Function of Targeted Histone Aceytltransferases in Yeast", The Journal of Biological Chemistry (2006), 281:3980-3988.
Yuan; et al. "Genome-scale identification of nucleosome positions in S. cerevisiae", Science (Jul. 2005), 309 (5734):626-630.

\* cited by examiner

NUCLEOSOME-EXCLUDING SEQUENCES (NES) AS A DNA SPACER IN VECTORS RESULTS IN PROLONGED TRANSGENE EXPRESSION IN EUKARYOTIC CELLS

GOVERNMENT RIGHTS

This invention was made with Government support under contract HL064274 awarded by the National Institutes of Health. The Government has certain rights in the invention.

BACKGROUND OF THE INVENTION

The treatment of a number of diseases can be achieved through gene therapy, where curative transgenes are introduced into a patient's cells by delivery with a vector of interest, for example viral, bacterial, mini-circle, etc. vectors. The delivered transgenes can integrate into the chromosomal DNA, replicate episomally or persist as non-replicating episomal elements in non-dividing cells. Depending on the properties of the transgene expression cassette, particular features of specific transgene integration sites and the state of the individual recipient cells, the transgenes are expressed with varying degree of efficiency. On some occasions, the transgenes are permanently silenced immediately after introduction, on other occasions transgene silencing occurs only after a certain period of adequate expression and on still other occasions transgene expression varies dramatically among the individual clones of transgene-harboring cells. Such variation is thought to be mainly due to the transgene's interaction with its immediate genetic neighborhood within the host genome. Stable long-term transgene expression in differentiating cells is particularly challenging. At a transcriptional level, the changing scenery of transcription initiation factor pools, chromatin re-modelling and DNA methylation events during differentiation contribute to the transiency of transgene expression.

Standard plasmid vectors composed of a transgene expression cassette and plasmid bacterial backbone (BB) DNA are able to express a high level of transgene product shortly after entering the cells, but the transgene product usually declines to very low or undetectable levels in a period of days even though the vector DNA is not lost. In fact, only very rare constructs in certain circumstances are able to express significant levels of transgene product for a prolonged period of time. There are a number of different factors (e.g., transgene product, mouse strain, and promoter) that may explain some of the variations in inter- and intralaboratory experimental results.

Early studies identified the nucleosome as the basic structural repeat unit of chromatin. It is composed of a nucleosome core containing 147 bp of DNA wrapped around a central histone octamer containing two molecules each of the four core histones (H2A, H2B, H3 and H4), and a "linker" DNA of characteristic length, which connects one nucleosome to the next. A single molecule of histone H1 (linker histone) is bound to the nucleosome at the point where the DNA enters and exits the core, and to the linker DNA. The DNA within the nucleosome core is protected from nucleases by the core histones, whereas the linker DNA is vulnerable to digestion. Thus, chromatin is composed of arrays of regularly spaced nucleosomes.

At a given moment in a cell population, there will be many possible chromatin states, including cells in which RNA polymerase II is initiating transcription at a nucleosome-free promoter, cells in which elongating RNA polymerase II is present at different places on the gene, causing local disruptions, and cells in which the gene is transiently in a non-transcribed state, or in the process of being remodeled. Thus, the combined effects of transcription and remodeling are expected to result in different chromatin structures at different times on the same gene. Many genes exhibit a sinusoidal nucleosome density profile, with peaks interpreted as positioned nucleosomes and troughs as linkers; many other genes exhibit more complex patterns that are difficult to interpret.

Methods of preventing transgene silencing from vectors introduced into cells are of great interest. The present invention addresses this issue.

SUMMARY OF THE INVENTION

Compositions and methods are provided for engineering vectors comprising transgenes, which vectors reduce silencing of the transgene expression after introduction into a target cell. Vectors of interest for engineering by the methods of the invention comprise non-coding (or spacer) DNA that is associated with transgene expression silencing, for example bacterial backbone sequences in plasmids, spacer DNA, particularly spacer DNA of greater than about 500 nucleotides in length, and the like. Vectors of interest include, in particular, any episomal vector, e.g. viral vectors, plasmid vectors, artificial chromosomes, mini-circles and the like. In the methods of the invention, a nucleosome excluding sequence (NES) is inserted into the sequence of the silencing DNA at intervals sufficient to reduce transgene expression silencing.

The methods of the invention find use in enhancing transgene expression in eukaryotic cells for various purposes, including target validation, research, therapeutics, etc. In some embodiments the cells are animal cells, including without limitation mammalian cells. In other embodiments the cells are plant cells, fungal cells, etc.

BRIEF DESCRIPTION OF THE DRAWINGS

FIG. 7. Sequence of human alphoid repeat DNA spacer used in the plasmid constructs in FIGS. 1 and 2.

FIG. 8. Sequence of random DNA spacer used in the plasmid constructs in FIGS. 3, 4, 5 and 6.

FIG. 10: Detailed sequence of 2.2 kb nucleosome exclusion sequence (NES). 20 bp of "T" were arranged in every 60 bp of random DNA.

DETAILED DESCRIPTION OF THE EMBODIMENTS

Figure 1:
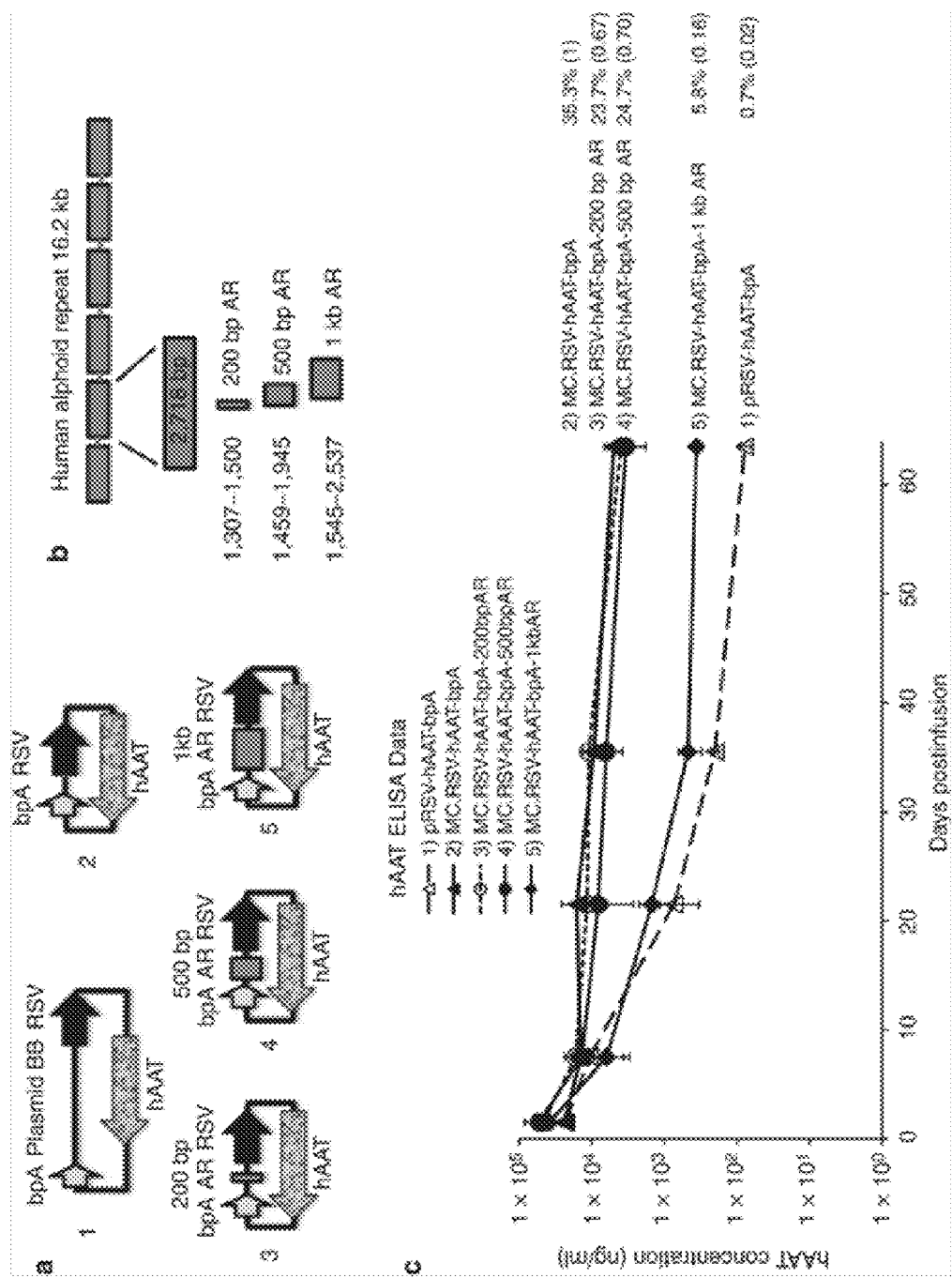
FIG. 1. RSV-hAAT expression cassette constructs and transgene expression in mice. (a) Schematic of DNA constructs containing the alphoid repeats (ARs) used for injections. (b) The schematic structure of human AR and spacers generated from this sequence. The 16.2 kb human AR DNA consists of six 2.7 kb repetitive DNA fragments. A 200 bp (from 1,307 to 1,500), a 500 bp (from 1,459 to 1,945), and a 1 kb (from 1,545 to 2,537) DNA spacers were generated from a single repetitive fragment of human AR (FIG. 7 for sequence details). These three spacer sequences partially overlap. However, within each spacer, no sequences are repetitive. These AR spacers were inserted between the 5' and the 3' ends of expression cassette in multiple DNA constructs pictured in a. (c) DNA constructs pictured in a were injected into C57BL/6 mice respectively (n=5 per group). Serum hAAT levels were determined over time. Two values are presented for each experimental group. The decay of hAAT expression is the level at the last time point/7-day level. The ratio of decay of expression for each transfection group/decay of expression for the corresponding minicircle transfection group (bracketed). If this ratio is <0.5, the transgene expression from a transfection group is defined as silenced. BB, backbone, ELISA, enzyme-linked immunosorbent assay; hAAT, human α1-antitrypsin.
Figure 2:
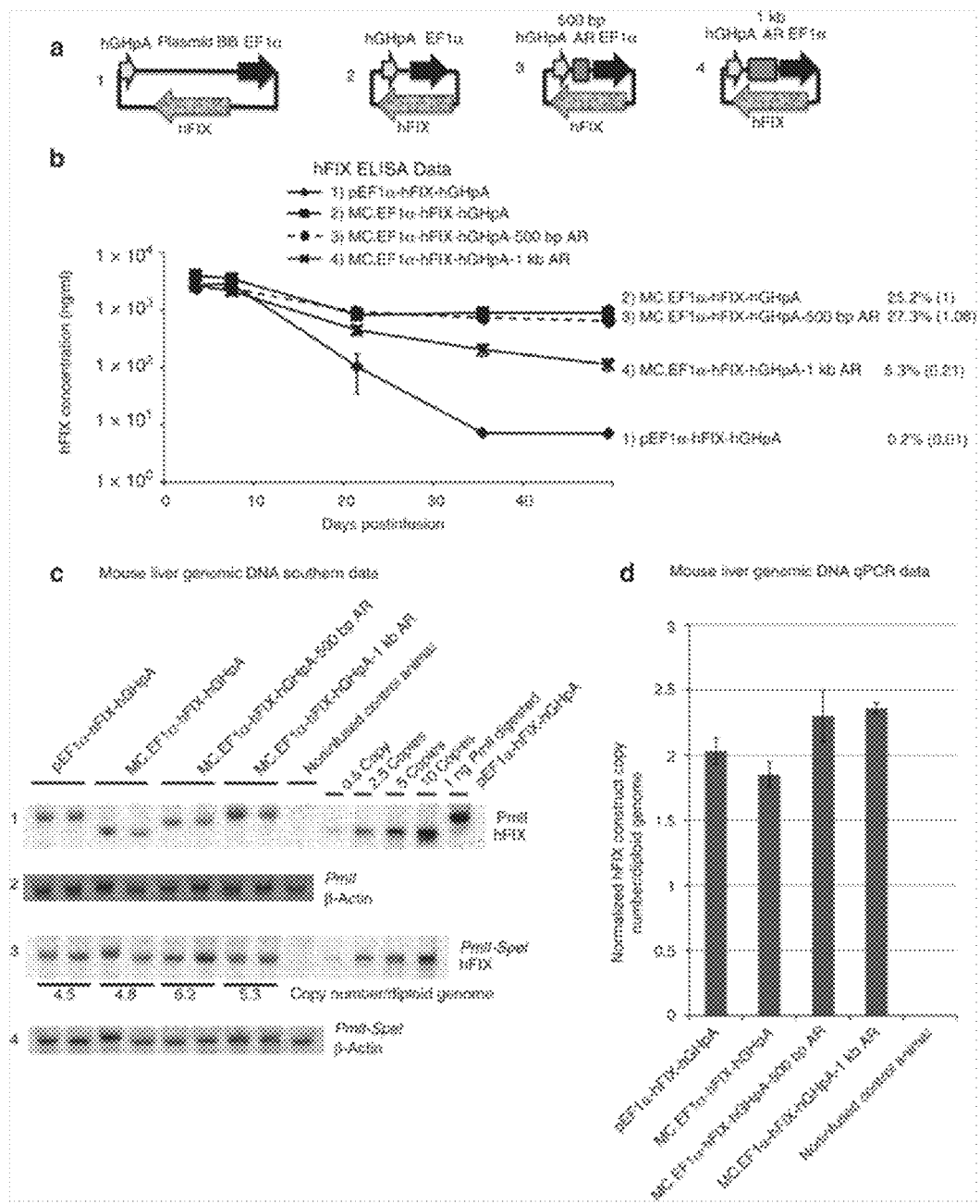
FIG. 2. EF1α-hFIX expression cassette constructs and transgene expression in mice. (a) Schematic representation of the DNA constructs containing the alphoid repeat (AR) sequences used in the studies. (b) The DNA constructs pictured in a were injected into C57BL/6 mice (n=per group). Plasma hFIX levels were determined over time. The provided values are as described in FIG. 1. (c) Mouse liver genomic DNA Southern blots from 49-day postinfusion liver genomic DNA samples (n=2 per group). Twenty microgram of each genomic DNA sample was digested with PmlI (row 1 and 2), or PmlI and SpeI (row 3 and 4) restriction enzymes to achieve single or double digestion of the infused DNA constructs, respectively; 0.5, 2.5, 5, and copies of PmlI-SpeI double digested 4.6 kb MC.EF1α-hFIX-hGHpA minicircle DNA were loaded together with 20 μg noninfused control genomic DNA as copy number control. Rows 1 and 3 were probed with [P-32] dCTP-labeled 1.4 kb hFIX cDNA. Rows 2 and 4 were probed with a [P-32] dCTP-labeled 300 bp β-actin. Row 1, PmlI digestion linearized 8 kb pEF1α-hFIX-hGHpA, 4.6 kb MC.EF1α-hFIX-hGHpA, 5.1 kb MC.EF1α-hFIX-hGHpA-500 bp AR, and 5.6 kb MC.EF1α-hFIX-hGHpA-1 kb AR. Row 3, PmlI-SpeI double digestion released a 4.6 kb fragment in all groups. The corresponding DNA vector copy number per diploid genome was indicated under each band. (d) Copy number of each construct per diploid genome in 49-day postinfusion liver samples were determined by quantitative real-time PCR. Standard deviations were based on two biological samples each performed in duplicate experiments (n=4). BB, backbone; ELISA, enzyme-linked immunosorbent assay; hFIX, human factor IX; qPCR, quantitative PCR.

Expression vectors for the introduction of a transgene into a cell are engineering to reduce transgene expression silencing, by the introduction of NES sequences into gene silencing regions of polynucleotides in the vector.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

A "gene silencing" sequence as used herein refers to a region of a vector polynucleotide, which can be DNA or RNA as appropriate, which region is outside of a coding sequence, and can be outside of an expression cassette, the presence of which results in a degradation of expression levels over time of transgene coding sequences present in the vector when the vector is introduced into a cell. The cell may be in vivo or in vivo. Degradation of expression, or silencing, is usually not linked to loss of copy number of the vector.

Silencing can be quantitated by measuring expression of the desired transgene product at an early time point, conveniently, for example at around day 3, 5, 7, etc., and a later time point, for example at day 10, 20, 30, 40 etc. A reduction of greater than about 50% is considered to reflect silencing of expression, e.g. 50%, 75%, 80%, 90%, 95% etc.

In some embodiments, a gene silencing sequence comprises at least about 400 bp, at least about 500 bp, at least about 1 kb, at least about 1.5 kb, at least about 2 kb or more of sequence outside of the transgene. In some embodiments the gene silencing sequence is comprised at least in part of bacterial plasmid backbone sequences. Such sequences can be required for manipulation and growth of plasmid in bacterial cells, e.g. origins of replication, drug resistance markers, phage integration sites, and the like, but are known to cause transgene silencing. However, as shown herein, eukaryotic genetic sequences can also cause silencing when positioned outside of the transgene.

As used herein, a nucleosome exclusion sequence, or NES, refers to an AT tract of at least about 15 nucleotides in length, at least about 18 nt. in length, at least about 20 nt. in length at least about 22 nt in length, at least about 25 nt in length, and may be not more than about 35 nt. in length, not more than about 30 nt. in length, not more than about 25 nt in length. In some embodiments an NES is substantially all A or T residues, i.e. not more than three G or C residues in the NES, not more than about two G or C residues, not more than one G or C residues, or no G or C residues.

The NES sequence can be substantially all A or all T residues, or may be mixed A and T, for example at a ratio on a single strand of about 1:20; 1:15; 1:10; 1:5; 1:2; 1:1 of A and T. It will be understood by one of skill in the art that as the two nucleotides are complementary, and the orientation is not critical, that a pure "A" tract will be complemented by a pure "T" tract, and thus the ratios are reversible.

An NES is inserted into a silencing region at intervals of about 50, about 60, about 70, about 80 nucleotides and up to about 250, about 200, about 150, about 100 nucleotides. Thus, a region is "unsilenced" by the introduction of about 10, about 12, about 15, about 18, about 20 NES insertions per 1 kb of silencing region.

Any convenient method can be used for introduction of the NES sequences, e.g. by recombinant methods, PCR, ligation, and the like as known in the art.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors.

An "expression cassette" comprises any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

Expression vectors will contain a promoter that is recognized by the host organism and is operably linked to a coding sequence of interest. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native reprogramming factor polypeptide promoter sequence and many heterologous promoters may be used to direct expression of a reprogramming factor polypeptide. However, heterologous promoters are preferred, as they generally permit greater transcription and higher yields. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself.

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA. Cells comprising the expression vector are grown under conditions that provide for expression of the desired polypeptide, either in vivo or in vitro.

A "minicircle" vector, as used herein, refers to a small, double stranded circular DNA molecule that provides for persistent, high level expression of a sequence of interest that is present on the vector, which sequence of interest may encode a polypeptide, an shRNA, an anti-sense RNA, an siRNA, and the like in a manner that is at least substantially expression cassette sequence and direction independent. The sequence of interest is operably linked to regulatory sequences present on the mini-circle vector, which regulatory sequences control its expression. Such mini-circle vectors are described, for example in published U.S. Patent Application US20040214329, herein specifically incorporated by reference.

Minicircle vectors differ from bacterial plasmid vectors in that they lack an origin of replication, and lack drug selection markers commonly found in bacterial plasmids, e.g. β-lactamase, tet, and the like. The minicircle may be substantially free of vector sequences other than the recombinase hybrid product sequence, and the sequence of interest, i.e. a transcribed sequence and regulatory sequences required for expression.

By "polynucleotide of interest" or "sequence of interest" it is meant any nucleic acid fragment adapted for introduction into a target cell. Suitable examples of polynucleotides of interest include promoter elements, coding sequences, e.g. therapeutic genes, marker genes, etc., control regions, trait-producing fragments, nucleic acid elements to accomplish gene disruption, as well as nucleic acids that do not encode for a polypeptide, including a polynucleotide that encodes a non-translated RNA, such as a shRNA that may play a role in RNA interference (RNAi) based gene expression control.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises at least about 50%, such as about 80%-85%; about 90-95%, as well as up to about 99% or more of the desired component. Techniques for purifying polynucleotides and polypeptides of interest are well-known in the art and include, for example, ion-exchange chromatography, affinity chromatography and sedimentation according to density.

The term "exogenous" is defined herein as DNA, such as the DNA constructs defined herein, which is artificially introduced into a cell, e.g. by the methods of the present invention. Exogenous DNA can possess sequences identical to or different from the endogenous DNA present in the cell prior to introduction by transfection, transformation, etc.

Methods of transfecting cells are well known in the art. By "transfected" it is meant an alteration in a cell resulting from the uptake of foreign nucleic acid, usually DNA. Use of the term "transfection" is not intended to limit introduction of the foreign nucleic acid to any particular method. Suitable methods include viral infection/transduction, conjugation, nanoparticle delivery, electroporation, particle gun technology, calcium phosphate precipitation, direct microinjection, and the like. The choice of method is generally dependent on the type of cell being transfected and the circumstances under which the transfection is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "coding sequence" or a sequence that "encodes" a selected polypeptide, is a nucleic acid molecule which is transcribed (in the case of DNA) and translated (in the case of mRNA) into a polypeptide, for example, when the nucleic acid is present in a living cell (in vivo) and placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral, eukaryotic, or prokaryotic DNA, and synthetic DNA sequences. A transcription termination sequence may be located 3' to the coding sequence, and a promoter may be located 5' to the coding sequence; along with additional control sequences if desired, such as enhancers, introns, poly adenylation site, etc. A DNA sequence encoding a polypeptide may be optimized for expression in a selected cell by using the codons preferred by the selected cell to represent the DNA copy of the desired polypeptide coding sequence.

The term "encoded by" refers to a nucleic acid sequence which codes for a polypeptide sequence. In addition, "encoded by" also refers to a nucleic acid sequence which codes for a non-translated RNA, such as a shRNA or antisense RNA, or other small RNA.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence. For example, intervening untranslated yet transcribed sequences can be present between the promoter sequence and the coding sequence and the promoter sequence can still be considered "operably linked" to the coding sequence.

"Target cell" as used herein refers to a cell that in which a vector is introduced for expression is desired. Target cells can be isolated (e.g., in culture) or in a multicellular organism (e.g., in a blastocyst, in a fetus, in a postnatal animal, and the like). Target cells of particular interest in the present application include, but not limited to, in vivo uses, e.g. liver cells, muscle cells including smooth, skeletal and cardiac muscle, pancreatic cells, neurons, cultured mammalian cells, including CHO cells, primary cell cultures such as fibroblasts, endothelial cells, etc., and stem cells, e.g. embryonic stem cells (e.g., cells having an embryonic stem cell phenotype), adult stem cells, pluripotent stem cells, hematopoietic stem cells, mesenchymal stem cells, and the like. Target cells also include plant cells, fungal cells, non-mammalian animals, and the like.

Methods

In the methods of the invention, a vector for transgene expression is designed or modified by introduction of NES sequences as described herein to reduce transgene silencing. The vector thus modified can be tested for transgene silencing by introduction of the vector into an appropriate cell, i.e. a cell where the transgene is expressed, and measuring expression over time, e.g. over about two weeks, three weeks, four weeks, etc. The methods of the invention reduce silencing, relative to an unmodified vector, by at least about 2-fold, 3-fold, 4-fold, 5-fold or more.

The vector thus modified can be introduced into a target cell by any appropriate method, and expressed in the target cell. Target cells include, without limitation, cells present in vivo, e.g. a mammal such as mouse, human, dog, cat, horse, pig, sheep, non-human primate, and the like. By reducing silencing, expression is maintained for an extended period of time relative to the unmodified vector.

In some embodiments, a composition is provided of a vector thus modified. In some embodiments a modified vector is a plasmid, a cosmid, a virus or virus-based vector, mini-circle, etc. In some embodiments a modified vector is provided in the absence of a transgene, for example with a linker for insertion of a desired transgene.

In some embodiments a kit is provided comprising a vector by introduction of NES sequences appropriately to reduce transgene silencing. The vector in such a kit can be provided without a transgene. Optionally a polylinker suitable for ease of introducing a transgene is provided, for example providing for operable linkage to a promoter, transcription terminator, enhancer, etc. as known in the art for expression of a desired gene. The vector may be provided lyophilized, in solution, etc., and may be accompanied by enzymes, buffers and the link suitable for introduction of a transgene into the vector; and or for introduction of the vector into a cell of interest. A kit may further comprise instructions for use, control sequences, assay reagents for measuring expression levels, and the like.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

A human alphoid repeat sequence (≥1 kb) can silence transgene expression from minicircle DNA in vivo. Although our previous studies have shown that covalent linkage of plasmid BB DNA to the transgene expression cassette is required for transgene silencing (Chen, Z. Y., et al. (2004). *Gene Ther* 11: 856-864), we wanted to establish if non-plasmid, non-prokaryotic DNA sequences placed between the 3' end of the expression cassette and 5' end of the enhancer/promoter would also silence the expression cassette. As shown in FIG. 1a, the promoter and terminator regions of the expression cassette are less than 50 bp apart in a minicircle vector. However, in plasmid DNA, the promoter and the terminator regions of gene expression cassette are separated by a plasmid BB of several kb in length. As shown in FIG. 1a 1-5, multiple minicircle vectors were generated containing different lengths of exogenous DNA derived from a 16.2 kb human alphoid repeat (AR) sequence. In the first set of studies, the human AR DNA fragment was chosen as the nonbacterial, noncoding, and nongenic spacer. This segment has previously been used as an inert stuffer sequence in viral-gene deleted recombinant adenoviruses (Ehrhardt, A., et al. (2002). *Blood* 99: 3923-3930). The 16.2 kb human AR DNA is a centromeric sequence isolated from human chromosome 17. This centromeric sequence consists of six 2.7 kb repetitive DNA fragments and contributes to but does not define centromeric function.

The first expression system tested was the human α1-antitrypsin (hAAT) cDNA driven by RSV-LTR promoter. We followed transgene expression levels over time using 7 days as the early time point to allow for steady state expression and eliminate variations in early expression due to the injection procedure. We calculate the decay of expression by calculating a ratio: transgene product level at any time point after day 7/day 7 level. Transgene silencing of a plasmid vector is defined when the decay of expression (at any time point after 7 days) for a plasmid vector/minicircle vector is <0.5. The minicircle, MC.RSV-hAAT-bpA minicircle and pRSV-hAAT-bpA plasmid (including a 3 kb bacterial BB sequence) were used as the non-silenced and silenced controls, respectively. As shown in FIG. 1b, 200 bp, 500 bp, and 1 kb spacers (FIG. 7 for sequence details) derived from the human AR DNA fragment were inserted in between the 5' end of RSV-LTR promoter and the 3' end of bovine poly A in MC.RSV-hAAT-bpA minicircle, respectively as marked in FIG. 1a 3-5. These minicircle constructs, MC.RSV-hAAT-bpA-200 bp AR, MC.RSV-hAAT-bpA-500 bp AR, and MC.RSV-hAATbpA-1 kb AR, and control DNAs were transfected into the liver of 6-8-week-old C57BL/6 female mice through a hydrodynamic tail vein injection. The transgene expression was quantified by enzyme-linked immunosorbent assay measurement of serum hAAT protein at various time points encompassing a 2-month interval (FIG. 1c). As previously shown, pRSV-hAAT-bpA was capable of expressing high levels of hAAT shortly after infusion, yet expression declined to very low levels during the next 2-3 weeks, while expression from MC.RSV-hAAT-bpA was more consistent throughout the duration of the experiment. The presence of 200 bp AR spacer and 500 bp AR spacer resulted in expression profiles similar to the minicircle whereas the 1 kb AR spacer resulted in high serum levels of hAAT signal at early time points, which rapidly declined providing an expression pattern similar to the silenced plasmid sequence (FIG. 1c).

To determine if these results were consistent with different expression cassettes, we utilized a second unrelated expression cassette, a human factor IX (hFIX) producing minicircle driven by the EF1-α promoter, MC.EF1α-hFIX-hGHpA, into which we inserted the 500 bp or 1,000 bp human AR spacers (FIG. 2a). As seen in FIG. 2b, animals infused with the controls, MC.EF1α-hFIX-hGHpA and pEF1α-hFIX-hGHpA (including a 3.5 kb bacterial BB sequence), had persistent and transient expression profiles, respectively. The MC.EF1α-hFIX-hGHpA-500 bp AR vector produced high and prolonged plasma hFIX levels similar to that observed with the minicircle vector, while the MC.EF1α-hFIX-hGHpA-1 kb AR was incapable of maintaining high level transgene expression in vivo. Therefore, the gene expression profiles from unrelated transgenes using the same nonbacterial spacers were concordant.

In our previous studies (Chen, Z. Y., et al. (2003). Mol Ther 8: 495-500) (Nakai, H., et al. (2001). J Virol 75: 6969-6976), we determined that plasmid/episomal DNA vectors remain episomal and that the relative concentrations of minicircle and plasmid DNAs remain similar over time. To confirm that the results obtained in these studies were similar to our previous studies and not due to differential loss of episomal DNA vectors, we performed both quantitative Southern blot analysis (FIG. 2c) and quantitative PCR (qPCR) assays (FIG. 2d) from the livers of treated animals 7 weeks after vector administration. Restriction enzyme digest that cut the vector once established that the bulk of the vector persisted as a monocircular episome, while a two-cut vector digest was used to quantify vector copy number (FIG. 2c). For all the plasmids tested, the vector copy number per diploid genome varied from 4.5 to 6.2 copies. qPCR estimated vector genome copies that ranged from 1.9 to 2.3 copies per diploid genome. These data establish that differences in vector copy are similar regardless of the vector tested and cannot explain the difference in transgene expression.

Random DNA sequences (1 kb) are capable of silencing transgene expression in vivo. DNA sequences obtained from the genome have evolved to serve specific functions. Thus, it is not possible to exclude that the nonarbitrary nature of any genome-derived sequence might have an influence on gene expression. To exclude the possibility of such bias, we used a spacer sequence, generated by a random enzymatic process (see Methods and FIG. 8). Five hundred by and 1 kb fragments were PCR amplified from the original 6.4 kb random sequence and then inserted into minicircle as spacers in between the 5' and 3' ends of each of the two transgene expression cassettes. In the first experiments, MC.RSVhAAT-bpA-500 bp RD and MC.RSV-hAAT-bpA-1 kb RD were compared with the control plasmid and minicircle DNAs. As indicated in FIG. 3b, minicircle with 500 bp random DNA (RD) spacer produced a transgene expression pattern similar to minicircle without spacer. However minicircle with 1 kb RD spacer exhibited a transgene expression pattern similar to plasmid DNA. Similar expression patterns were also obtained when a second expression cassette, EF1α-hFIX-hGHpA (FIG. 4) with the various spacers were compared. In the presence of the 1 kb RD spacer, MC.EF1 α-hFIX-hGHpA-1 kb RD resulted in short-lived expression whereas the MC.EF1 α-hFIX-hGHpA-500 bp RD treated animals maintained high levels of plasma hFIX for at least 2 months. Again to establish that the loss of trangene expression was not due to differential plasmid loss, we quantified the vector DNAs by qPCR assays (FIG. 3c). Concordant with the experiments in FIG. 2, the vector copy numbers were similar between groups varying by less than two times (1.8-3.0 copies per diploid genome). To determine if transgene silencing was due to differential levels of the RNA transcript, hAAT messenger RNAs were quantified by reverse transcription (RT)-PCR. As shown in (FIG. 3d), the hAAT transcript levels correlated with the level of protein expression. The MC.RSV-hAAT-bpA and MC.RSVhAAT-bpA-500 bp RD infused groups had about five times higher amounts of transcript compared to the MC.RSV-hAAT-bpA-1 kb RD infused animals while the pRSV-hAAT injection more than a 10 times lower amount of transcript compared to the minicircle or MC.RSV-hAAT-bpA-500 bp RD injected groups.

Figure 5:
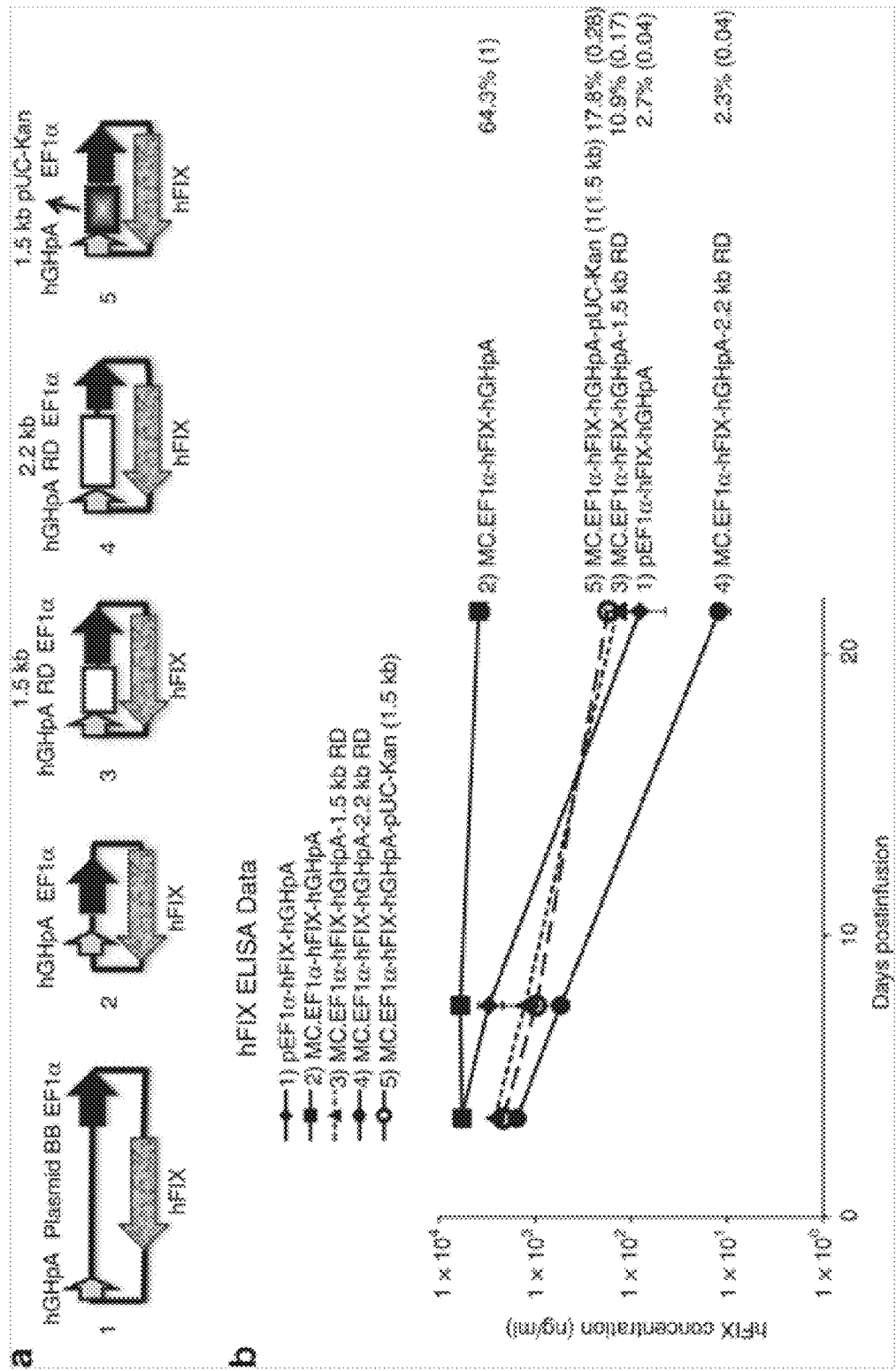
FIG. 5. EF1α-hFIX constructs and transgene expression in mice. (a) Schematic of DNA constructs containing large random DNA (RD) spacers. (b) DNA constructs in a were injected into C57BL/6 mice respectively (n=5 per group). Plasma hFIX levels were determined over time. The provided values are as described in FIG. 1. BB, backbone; ELISA, enzyme-linked immunosorbent assay; hFIX, human factor IX.

We further tested whether spacers containing larger spacer inserts (>1 kb) would have stronger effects on silencing minicircle and plasmid DNA transgene expression in vivo; 1.5 kb and 2.2 kb RD fragments were used to generate MC.EF1α-hFIX-hGHpA-1.5 kb RD and MC.EF1α-hFIX-hGHpA-2.2 kb RD vectors. The 1.5 kb and 1 kb sequences only share a 400 bp stretch (FIG. 8). Mice that infused with these constructs also resulted in transgene silencing (FIG. 5).

Taken together these results provide strong evidence that the extragenic DNA spacer length between the 5' and 3' ends of an expression cassette and not the specific DNA sequence or structure derived from a bacterial plasmid BB DNA is the important parameter dictating whether or not a plasmid DNA will be silenced.

Figure 3:
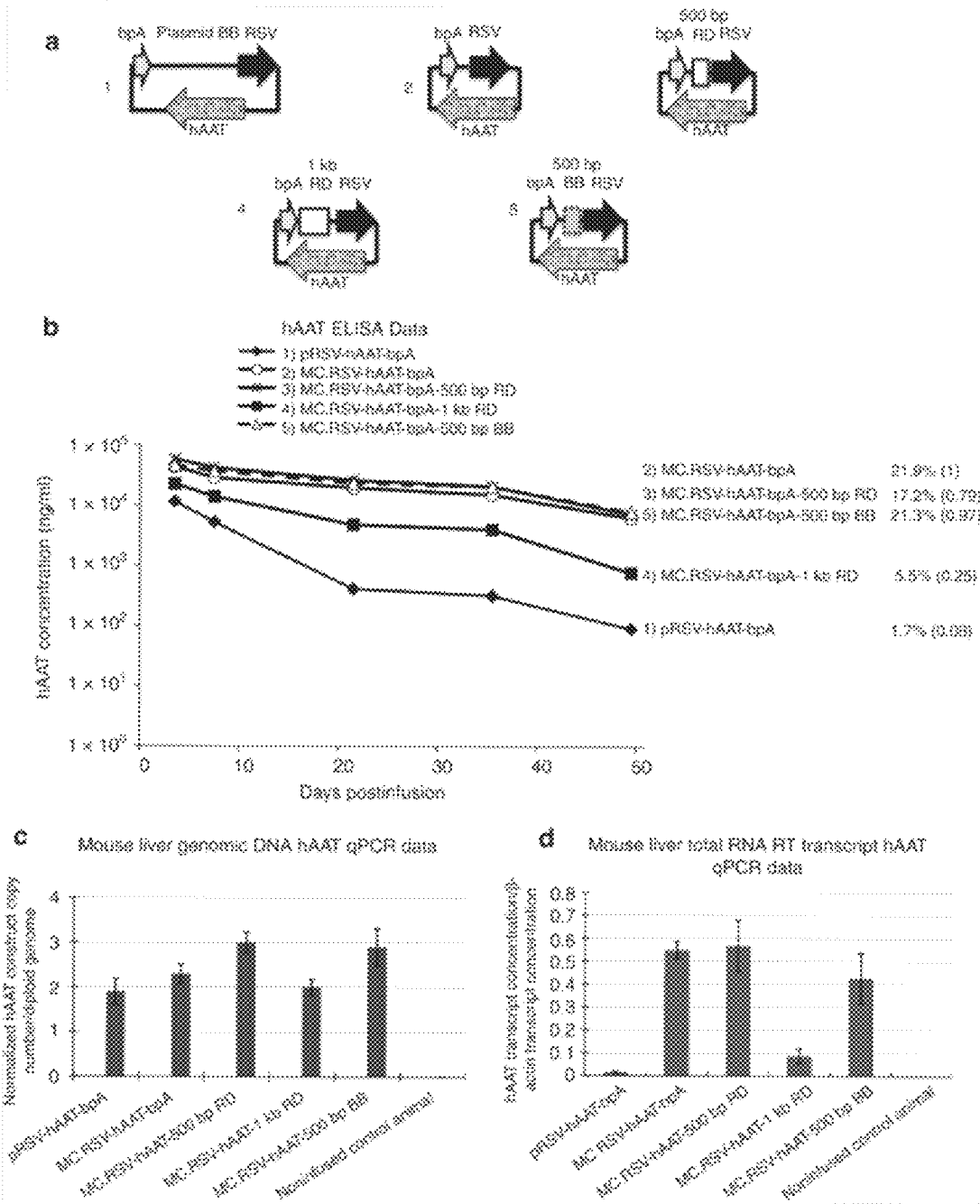
FIG. 3. RSV-hAAT expression cassette constructs and transgene expression in mice. (a) Schematic of the DNA constructs containing random DNA (RD) or bacterial backbone (BB) used as spacers. (b) DNA constructs from a were injected into C57BL/6 mice (n=5 per group). Serum hAAT levels were determined over time. The provided values are as described in FIG. 1. (c) Vector DNA copy number (per diploid genome) and (d) Normalized hAAT mRNA transcript levels in 49-day postinfusion liver samples. In c and d, standard deviations were based on two biological samples each performed in duplicate experiments (n=4). ELISA, enzyme-linked immunosorbent assay; hAAT, human α1-antitrypsin; mRNA, messenger RNA; qPCR, quantitative PCR; RT, reverse transcription.
Figure 4:
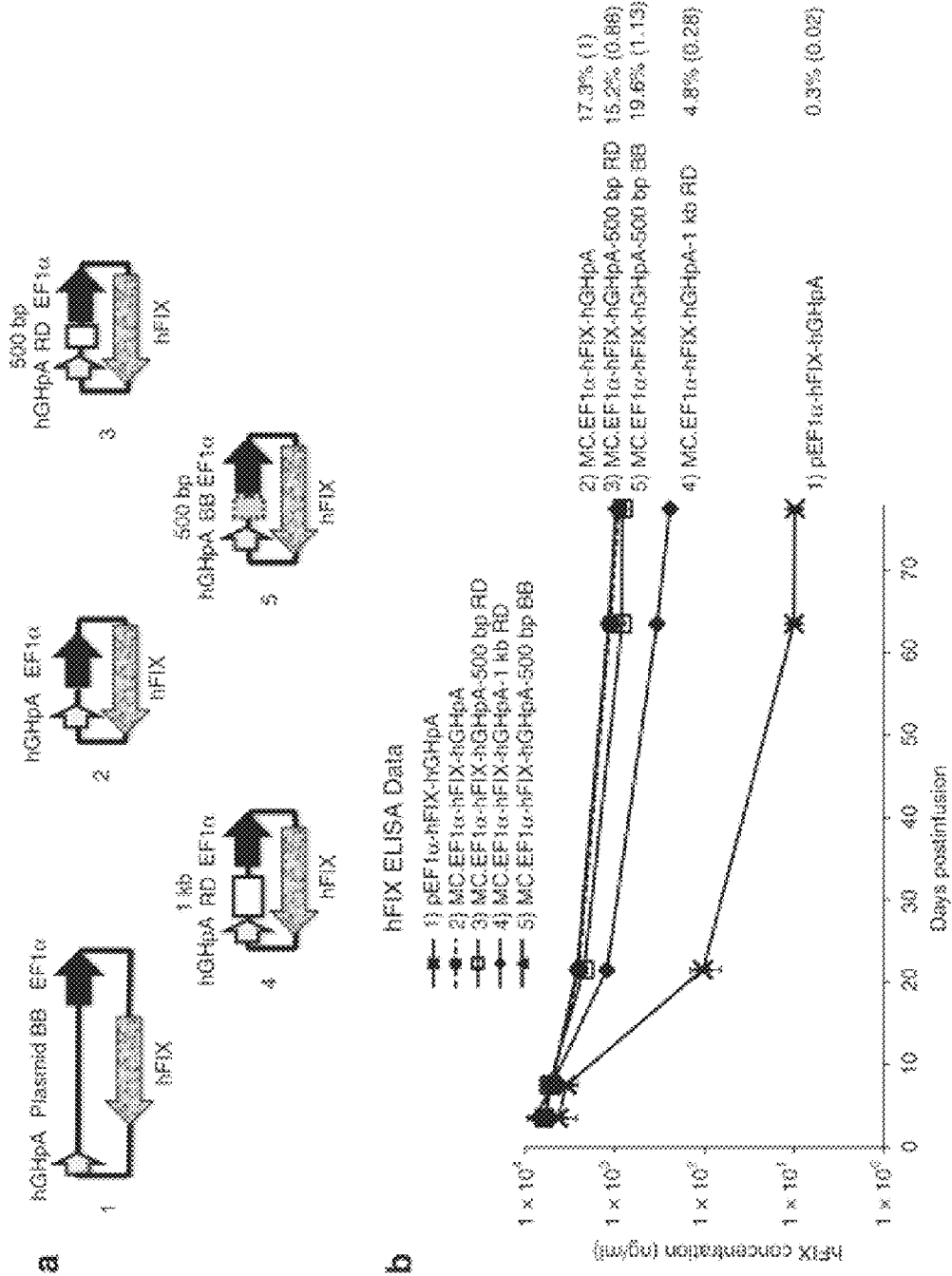
FIG. 4. EF1α-hFIX expression cassette constructs and transgene expression in mice. (a) Schematic of hFIX expressing DNA constructs with random DNA (RD) or bacterial backbone (BB) as spacer. (b) Constructs in a were injected into C57BL/6 mice (n=5 per group). Plasma hFIX levels were determined over time. The provided values are as described in FIG. 1. ELISA, enzyme-linked immunosorbent assay; hFIX, human factor IX.

Short plasmid BB sequences inserted as spacers are incapable of silencing trangene expression in vivo while longer plasmid BB sequences silence the transgene. Previously, we have substituted various prokaryotic antibiotic resistance genes and/or various plasmid origins of replication, and eliminated non-essential plasmid BB sequences but transgene silencing still occurred regardless of the specific substitutions. In all cases, the plasmid BB was well over 1 kb. To further test the hypothesis that the bacterial plasmid BB DNA does not contain silencing favorable sequences, we constructed minicircles containing a 500 bp pUC-derived bacterial plasmid origin of replication in either the hFIX or hAAT expression cassette (FIGS. 3 and 4). As shown in FIGS. 3 and 4, 500 bp BB spacer failed to silence either the hAAT or hFIX transgene expression cassettes in vivo. This result confirmed that generic plasmid origin sequence is not sufficient for transgene silencing in DNA plasmid vectors. On the other hand, when a fragment of a BB—a 1.5 kb BB containing pUC origin and kanamycin resistance gene was placed in between the 5' and 3' ends of the hFIX expression cassette (MC.EF1α-hFIX-hGHpA-pUC-Kan (1.5 kb)), transgene expression was silenced (FIG. 5). This was consistent with our other results that longer extragenic spacer (1 kb) was sufficient to silence the transgene and supporting the idea that the length of the DNA insert and not anything specific about the bacterial plasmid DNA itself was the critical determinant responsible for transgene silencing.

Figure 6:
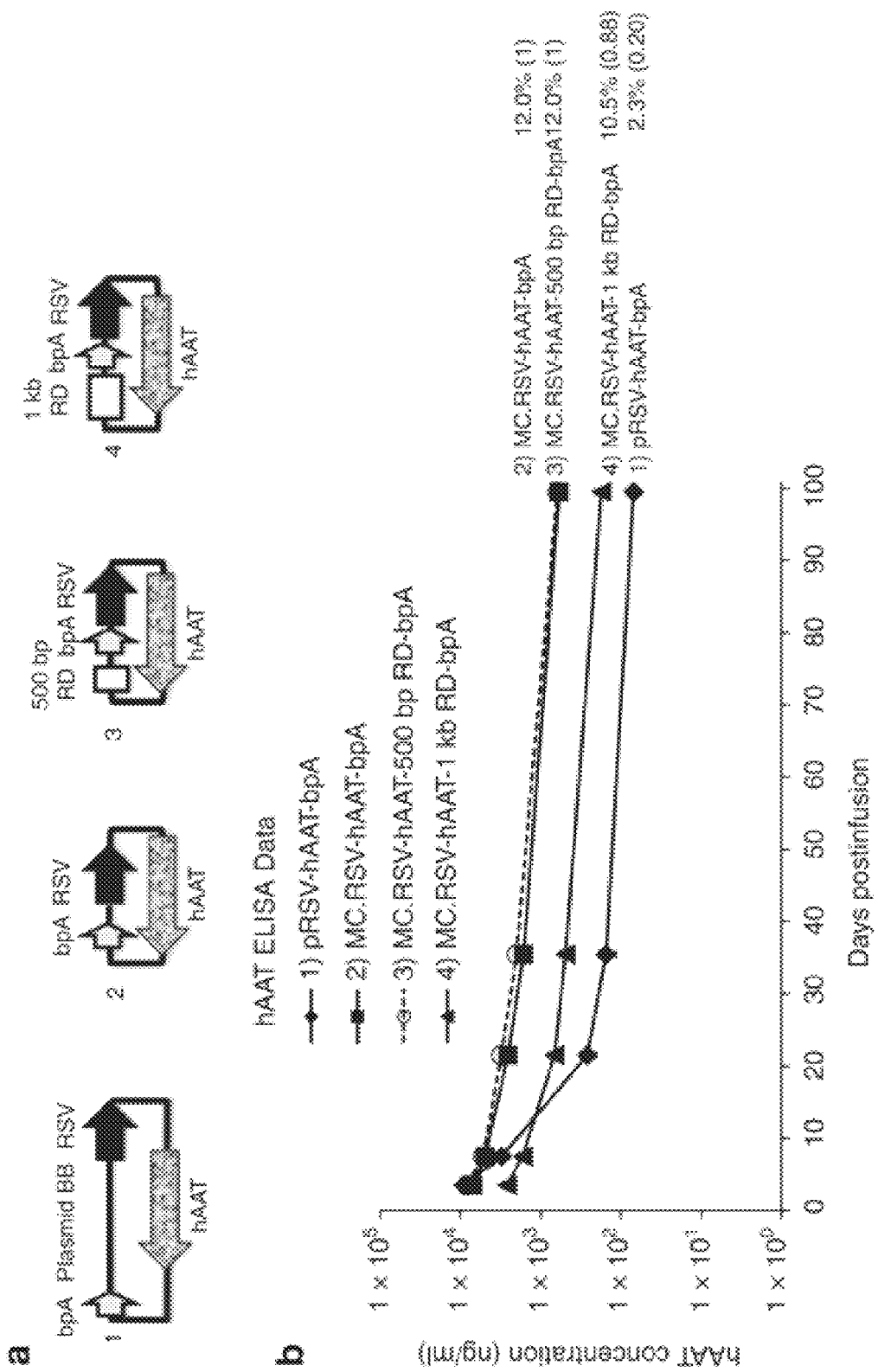
FIG. 6. RSV-hAAT expression cassette constructs containing extended 3'UTRs and transgene expression in mice. (a) Schematic of DNA constructs containing extended 3'UTRs. (b) DNA constructs in a were injected into C57BL/6 mice respectively (n=5 per group). Serum hAAT levels were determined over time. The provided values are as described in FIG. 1. BB, backbone; ELISA, enzyme-linked immunosorbent assay; hAAT, human α1-antitrypsin; UTR, untranslated region.

DNA spacers placed into the 3'UTR do not silence minicircle transgene expression in vivo. In all of the above experiments, spacers were placed into the extragenic region of the DNA vector. We wanted to establish if the same DNA spacers placed within the transcription unit would still silence the plasmid vector. Such studies would test whether: (i) the DNA sequences could influence silencing independent of their context; (ii) establish if the total length of the vector affected silencing; (iii) establish if the length of the noncoding extragenic region affected silencing. To address these questions, 500 bp and 1 kb RD spacers were placed between the stop codon of hAAT transgene and the polyA signal, making the inserted segment a part of the 3'-untranslated region (UTR) sequences in MC.RSVhAAT-500 bp RD-bpA and MC.RSV-hAAT-1 kb RD-bpA (FIG. 6a). These constructs were tested in animals for hAAT expression in vivo. Results from animal test indicated that neither 500 by RD and 1 kb RD when placed next to stop codon of hAAT induced transgene silencing (FIG. 6b). We note that the 1 kb RD resulted in lower levels of initial transgene expression, but that this level was maintained and not silenced. Altering the 3'UTR sequence can greatly influence transgene expression with the addition of sequences generally resulting in reduced expression (Grzybowska, E. A., et al. (2001). Biochem Biophys Res Commun 288: 291-295). Therefore, the low initial expression was not unexpected.

Particularly striking in this study was the observation that the 1 kb RD sequences that induced silencing when placed outside of the transgene expression cassette did not induce silencing when contained within the 3'UTR. This provides further support that the spacer length and not the sequence itself located between the 5' and 3' ends of the expression cassette as a key determinant of persistent transgene expression in vivo.

In this study, we provide strong evidence that transgene-induced silencing is not restricted to the covalent attachment of plasmid bacterial BB sequences. Rather noncoding, nonbacterial, and nongenic DNA sequences reaching 1 kb or more in length regardless of their origin can also silence transgene expression. The sequences themselves were not inhibitory because if they were placed into the expression cassette such that it became part of the 3'UTR, silencing was not observed. The finding that extragenic spacer length rather than DNA type is the major factor influencing transgene silencing from plasmid DNA-based vectors provides important insights into mechanism.

Our results confirming that the messenger RNA and not vector DNA levels correlate with the amount of transgene protein strongly suggest that silencing is related to differences in transcription. Naked episomal DNA vectors undergo chromatinization after transfection of mouse liver. Moreover, ChIP analyses performed on chromatized plasmid and minicircle DNAs isolated from mouse liver established a good correlation between specific modified histones and the degree of transgene expression.

Materials and Methods

RD synthesis. We prepared a population of extended double-stranded DNa molecules of arbitrary sequence as follows. A random hexanucleotide mixture (dNdNdNdNdNdN; 5' and 3' OH, 100 ng in 50 µl) was reacted with bovine terminal transferase (17 units; US Biochemical, Cleveland, Ohio) for 4 hours at 37° C., followed by two rounds of addition of an additional aliquot of terminal transferase (17 units) and a 16 hour incubation at 37° C. Reaction conditions were 100 mmol/l sodium cacodylate pH 6.8, 1 mmol/l cobalt chloride, 0.1 mmol/l dithiothreitol, 4 mmol/l MgCl2, 1.2 mmol/l each of dATP, dTTP, dCTP, dGTP. Twelve units of pyrophosphatase were added at the beginning of the reaction to avoid accumulation of inhibitory pyrophosphate species. This reaction led to the synthesis of single-stranded DNA with lengths ranging from several 100 to several 1,000 bases, visible upon analytical agarose gel electrophoresis of an aliquot (3 µl) in the presence of 0.3 µg/ml ethidium bromide. Following the confirmation of a DNA population on ethidium visualization, a second strand was synthesized through the action of *Escherichia coli* DNA polymerase I as follows: 25 µg glycogen and 340 µl of 20 mmol/l Tris-HCl pH 7.5, 1 mmol/l EDTA, 10 mmol/l MgCl2, 1 mmol/l dithioerythritol, 500 µmol/l each dTTP, dCTP, dATP, dGTP were added, followed by addition of 45 units of *Escherichia coli* DNA polymerase I holoenzyme, sequential incubations for 20 minutes each at 4° C., 16° C., 23° C., addition of 20 additional units of *Escherichia coli* DNA polymerase I, and incubation at 37° C. for 2 hours. Reactions were then cleaned up by addition of 15 µl of 0.5 mol/l EDTA, 40 µl of 10 mol/l NH4OH pH 7.5, followed by extraction with phenol/CHCl3 (1:1; 400 µl), CHCl3 (400 µl) ethanol precipitation, and resuspension in 20 µl of 10 mmol/l Tris-HCl pH 7.5, 1 mmol/l EDTA. Following digestion of these samples with KpnI and XbaI, fragments were inserted into a KpnI+XbaI cut plasmid vectors and sequenced. A series of inserts were then combined using flanking sites to produce the extended random insert described. The RD sequence is listed in detail in FIG. 8. Sequences added to the vectors were examined and shown to lack a cryptic splice site. The absence of an additional polyadenylation site was confirmed by the lack of an AAUAAA sequence.

Vector construction. The pRSV-hAAT-bpA (Chen, Z. Y., et al. (2003). *Mol Ther* 8: 495-500) and pEF1α-hFIX-hGHpA (Chen, Z. Y., et al. (2004). *Gene Ther* 11: 856-864) plasmids were previously described. The hAAT and hFIX minicircle producing plasmids, pMC.RSV-hAAT-bpA and pMC.EF1α-hFIX-hGHpA, were engineered with a unique SpeI restriction enzyme site right after the polyA tail sequence. Multiple sized spacers were amplified from human AR sequence and RD sequences by PCR using primers containing the SpeI restriction enzyme digestion site at the 5' end. The correct PCR products were digested with SpeI and ligated to SpeI digestion linearized antarctic phosphatase treated pMC.RSV-hAAT-bpA and pMC.EF1α-hFIX-hGHpA.

The ligation solution was transformed into DH10B competent cells and grown on kanamycin selection agar plates at 37° C. overnight. DNA was isolated from selected colonies and retransformed into minicircle producing bacterial strain 10P3S2T and minicircle preparation.

Production of minicircle. Minicircle DNA was produced using a previously developed protocol (Kay, M. A., et al. (2010). *Nat Biotechnol* 28: 1287-1289). Early on day 1, cells were grown from one parental plasmid-transformed colony in 5 ml of Luria-Bertani broth containing 50 µg/ml kanamycin at 37° C. with shaking at 250 rpm. Later that evening, 100 µl of the 5 ml Luria-Bertani broth from the culture was added to 400 ml Terrific broth containing 50 µg/ml kanamycin and incubated at 37° C. with shaking at 250 rpm for 16-18 hours. The overnight culture's OD600 reading was between 3.75-4.25. The pH reading of the overnight culture was pH 6.5. The overnight culture was mixed with 400 ml fresh Luria-Bertani broth, 16 ml of 1 N NaOH and 0.4 ml of 20% L-arabinose, incubated at 32° C. with shaking at 250 rpm for 5 hours. Bacteria were pelleted and minicircles were isolated using a Qiagen mega plasmid kit (Qiagen, Valencia, Calif.) according to manufacturer's protocol with the exception that double the volume of P1, P2, and P3 buffers was used.

Animal studies. The animal experiments were done with approval from the Administrative Panel on Laboratory Animal Care at Stanford University and conformed to the guidelines set forth by the National Institutes of Health. Six- to 8-week-old female C57BL/6 mice purchased from Jackson Laboratory (Bar Harbor, Me.) were used for DNA injection. To ensure the same molar amount of DNA was injected into each animal, 3.63 µg/kb DNA was used for various sized constructs. For example, 8 µg (3.63 µg/kb×2.2 kb) DNA was used for 2.2 kb MC.RSV-hAAT-bpA constructs to inject each animal. Each DNA construct was diluted into 1.8 ml of 0.9% NaCl for each animal, and was delivered through hydrodynamic tail vein injection. Five animals were tested for each DNA construct in each tested experimental group. After DNA infusion, blood samples were collected periodically by a retro-orbital technique. The serum hAAT and plasma hFIX were quantitated by enzyme-linked immunosorbent assay.

Southern blot analysis of vector DNA structure in mouse liver. Liver genomic DNA was extracted through a salt-out procedure. Twenty microgram liver genomic DNA of each sample was digested with either PmlI alone or both PmlI and SpeI overnight at 37° C. PmlI cut the expression cassette once. PmlI-SpeI double digestion cut the expression cassette twice. Various copy numbers of MC.EF1α-hFIX-hGHpA vector DNA was also digested with PmlI and SpeI, and then mixed with 20 µg non-infused mouse liver genomic DNA in each lane as copy number control. PmlI digested pEF1α-hFIX-hGHpA vector DNA was also loaded along with 20 µg noninfused mouse liver genomic DNA as a size control for 8 kb band. Vector DNA copy number was calculated based on Applied Biosystems's method, http://www6.appliedbiosystems.com/support/tutorials/pdf/quant-per.pdf and by using internet tool http://www.uri.edu/research/gsc/resources/cndna.html. Digested DNA samples were separated by electrophoresis in 1% agarose gel and blotted onto a nitrocellulose membrane. Southern blot membrane was hybridized with [P-32] dCTP-labeled 1.4 kb hFIXcDNA, and [P-32] dCTP-labeled 300 bp β-actin (PCR product by using forward primer 5'ACGCGTCCAATTGC-CTTTCT3' and reverse primer 5'CTCGAGGTT-GAAGGTCTCAA3'). hFIX and β-actin signals were detected through phosphoimaging. The Southern blot signal strength was measured by Quantity One. hFIX signal was normalized to β-actin signal. Normalized hFIX signal was compared with copy number standard to obtain corresponding DNA vector copy number per diploid.

qPCR analysis of vector DNA structure in mouse liver. A 100 ng double-digested genomic DNA (PmlI-SpeI for FIG. 2 and XbaI-SpeI for FIG. 3*d*) from each sample was used as the template for qPCR. Or, 1 µl of RT reaction was used as template for FIG. 3*c*. Two animal samples from each injection group were selected and two 15 µl reactions were performed for each animal sample. Various copy numbers (2×10⁸ copies to 20 copies) of double-digested standard vector DNA along with 100 ng non-infused control genomic DNA per reaction was used to make copy number standard curve. Forward primer 5'ACATTGCCCTTCTGGAACTG3' and reverse primer 5'GCTGATCTCCCTTTGTGGAA3' oligos were used to amplify 150 bp fragment from hFIX cDNA region. Forward primer 5'AAGGCAAATGGGAGA-GACCT3' and reverse primer 5'TACCCAGCTGGACA-GCTTCT3' oligos were used to amplify 150 bp fragment from hAAT cDNA region. Forward primer 5'TTGCT-GACAGGATGCAGAAG3' and reverse primer 5'TGATC-CACATCTGCTGGAAG3' oligos were used to amplify 150 bp fragment from β-actin as loading control. The tested transgene signal was then normalized to the β-actin signal. The mass of a single diploid copy of mouse genome is 5.88 pg. Thus 100 ng genomic DNA contains 17,007 copies of diploid genome (1×10⁶ pg/5.88 pg). The average transgene copy number in 100 ng genomic DNA from each group was then divided by 17,007 to achieve the transgene construct copy number in each cell. All calculations were based on methods described by Applied Biosystems-method http://www6.appliedbiosystems.com/support/tutorials/pdf/quant_per.pdf and by using internet tool http://www.uri.edu/research/gsc/resources/cndna.html. qPCR was performed by using Corbett Research RG6000 PCR machine (Corbett Research, Mortlake, Australia).

RT and following qPCR analysis. Five microgram DNase I treated liver total RNA sample was used for each RT reaction with oligo(dT). The RT reaction was performed as described in the manual of SuperScript III RTS First-Strand cDNA Synthesis Kit from Invitrogen (Carlsbad, Calif.). Non-RT control of each sample was also performed; 1 µl RT or non-RT reaction was used as template for the following qPCR analysis. Each RT or non-RT sample was amplified by hAAT qPCR oligos and β-actin qPCR oligos as described above. The obtained hAAT signal was normalized by β-actin signal and the normalized hAAT signal from different vector infused animals were compared.

Example 2

3'UTR Sequences Prevent Silencing when Used as Spacer

Figure 9:
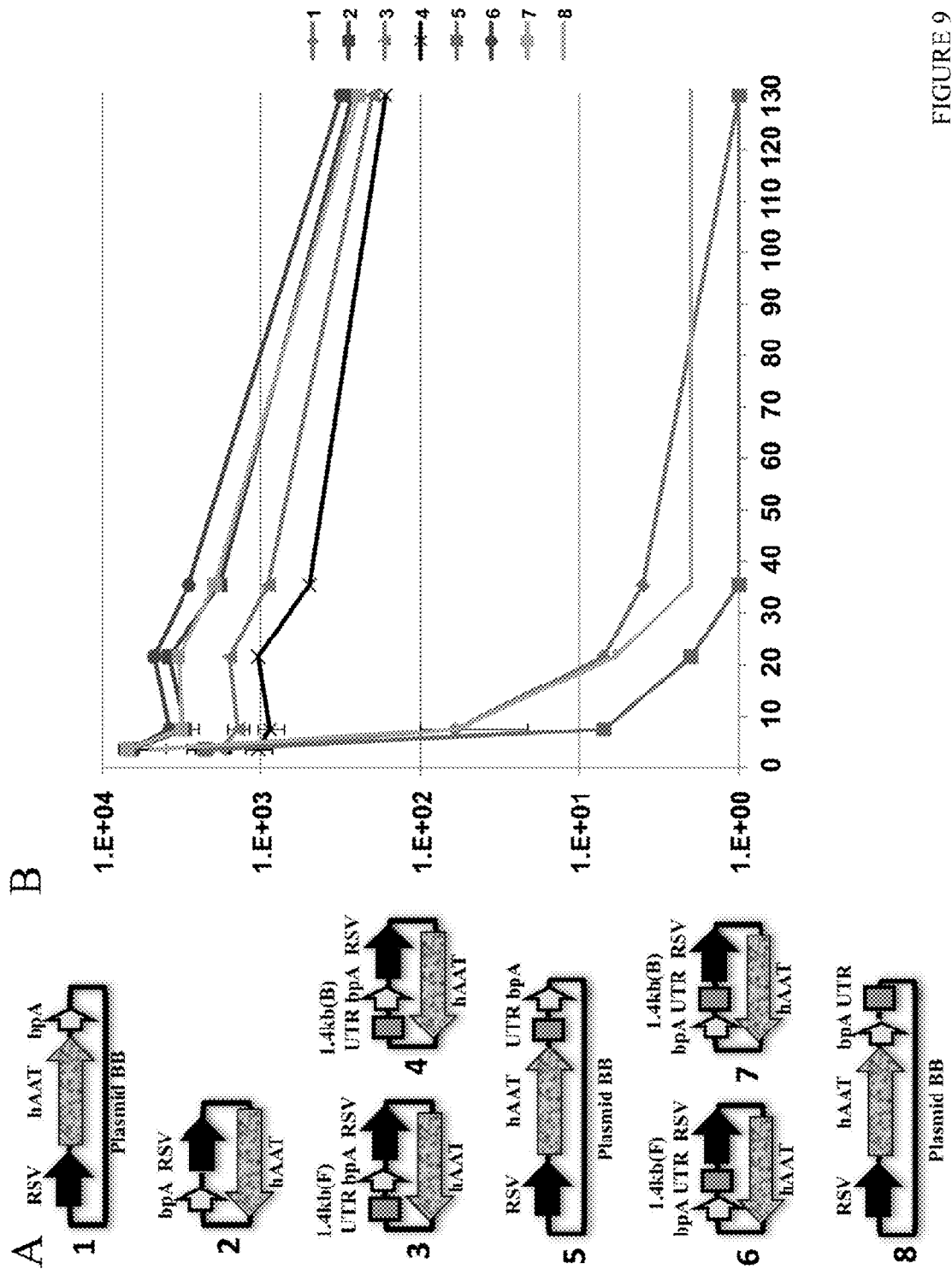
FIG. 9: RSV-hAAT (Rous arcoma virus promoter-human alpha 1-antitrypsin) expression constructs and transgene expression in mice. A) Schematic of hAAT expressing DNA constructs. A 1.4 kb human factor IX(hFIX) 3'UTR (UTR) sequence was placed before or after bpA sequence as spacer. This spacer was placed in either forward (F) or backward (B) orientation. B) Serum hAAT levels at various time points after equimolar infusion of one of the plasmid vectors were infused. (n=5/group). Error bars represent the standard deviation. This figure indicates that 1.4 kb hFIX 3'UTR doesn't silence transgene expression when used as spacer and this effect is orientation independent.

The data in Example 1 demonstrate that spacer DNA reaching 1 kb or more in length regardless of their origin can silence transgene expression. To further verify whether this is a general rule, DNA sequences from the expression cassette were used as spacer. In order to restrict the spacer sequences to noncoding and nonbacterial sequences, the 1.4 kb human factor IX (hFIX) 3'UTR sequence was tested for its ability to silence transgene as spacer. As shown in FIG. 9, expression constructs were designed and tested for transgene expression using this 1.4 kb hFIX 3'UTR as spacer before or after bpA sequence. This spacer was placed in either forward (F) or backward (B) orientation. Interestingly, although this 3'UTR sequence is longer than 1 kb, when placed as spacer at either orientation, it did not silence transgene expression.

As the first tested non-silencing large (>1 kb) spacer, hFIX 3'UTR has the opposite function in transgene expression comparing with human AR sequence, RD sequence and BB sequence when placed as spacer. Thus the specific sequence features of 3'UTR might contribute to this non-silencing phenomenon. One commonly agreed sequence characteristic of 3'UTR is the high NT content in these sequences and these A/T nucleotides usually arranged in long tracts.

The nucleosomes are the basic building blocks of eukaryotic chromatin. One nucleosome core particle consists of about 147 bp of DNA wrapped in left-handed suprahelical turns around a histone octamer containing two copies of each core histones H2A, H2B, H3 and H4. Nucleosomes are connected by short stretches of linker DNA (0-80 bp) at a fixed distance between them.

A-tracts, T-tracts, straight and rigid sequences that cause a sharp bend in the dinucleotide step following them, are strong nucleosome breakers and appear to be used as part of a nucleosome prevention system Oyer and Struhl 1995). The role of A-tracts in increasing transcription and protein accessibility has been well demonstrated (Russell et al. 1983; Struhl 1985; Chen et al. 1987), and nucleosome-free regions have been found to be enriched for A-tracts (Yuan et al. 2005).

Since the 3'UTR sequences are enriched in A/T nucleotides and these nucleotides are usually arranged in tracts, this special arrangement of long tract of A/T nucleotides may contribute to exclude nucleosome binding to the DNA. The non-silencing effect of 3'UTR spacer is orientation independent. This indicates the A/T nucleotides or tracts may have the same function in regulating transgene expression as spacer.

Example 3

Figure 10:
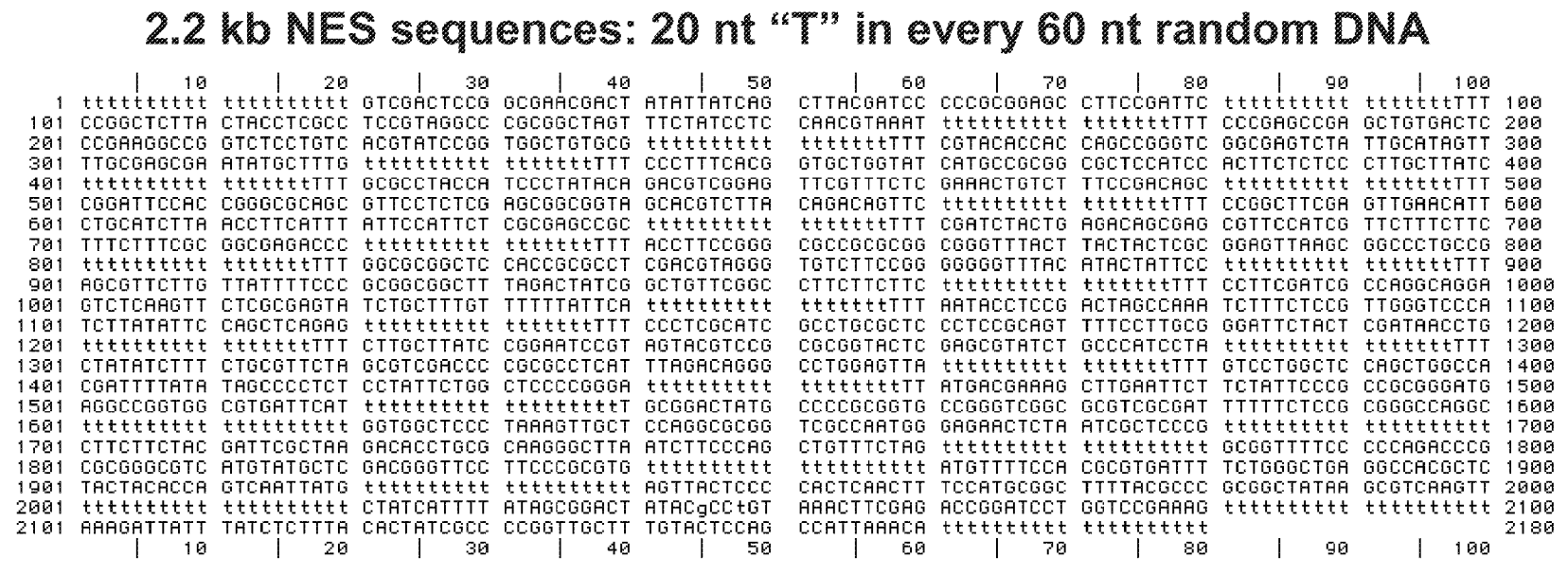

Synthesized Nucleosome Exclusion Sequences (NES) Persistent Transgene Expression when Used as Spacer Since poly A or poly T tracts can exclude nucleosomes Oyer and Struhl 1995, Segal E et al. 2009), it is possible that the NT enriched 3'UTR sequence can exclude nucleosome and therefore retains transgene expression. To prove this idea, we synthesized a 2.2 kb NES sequence and tested it effect in transgene silencing in vivo. As shown in FIG. 10, the NES sequence was made by putting 20 bp of "T" tracts in every 60 bp of random DNA.

Figure 11:
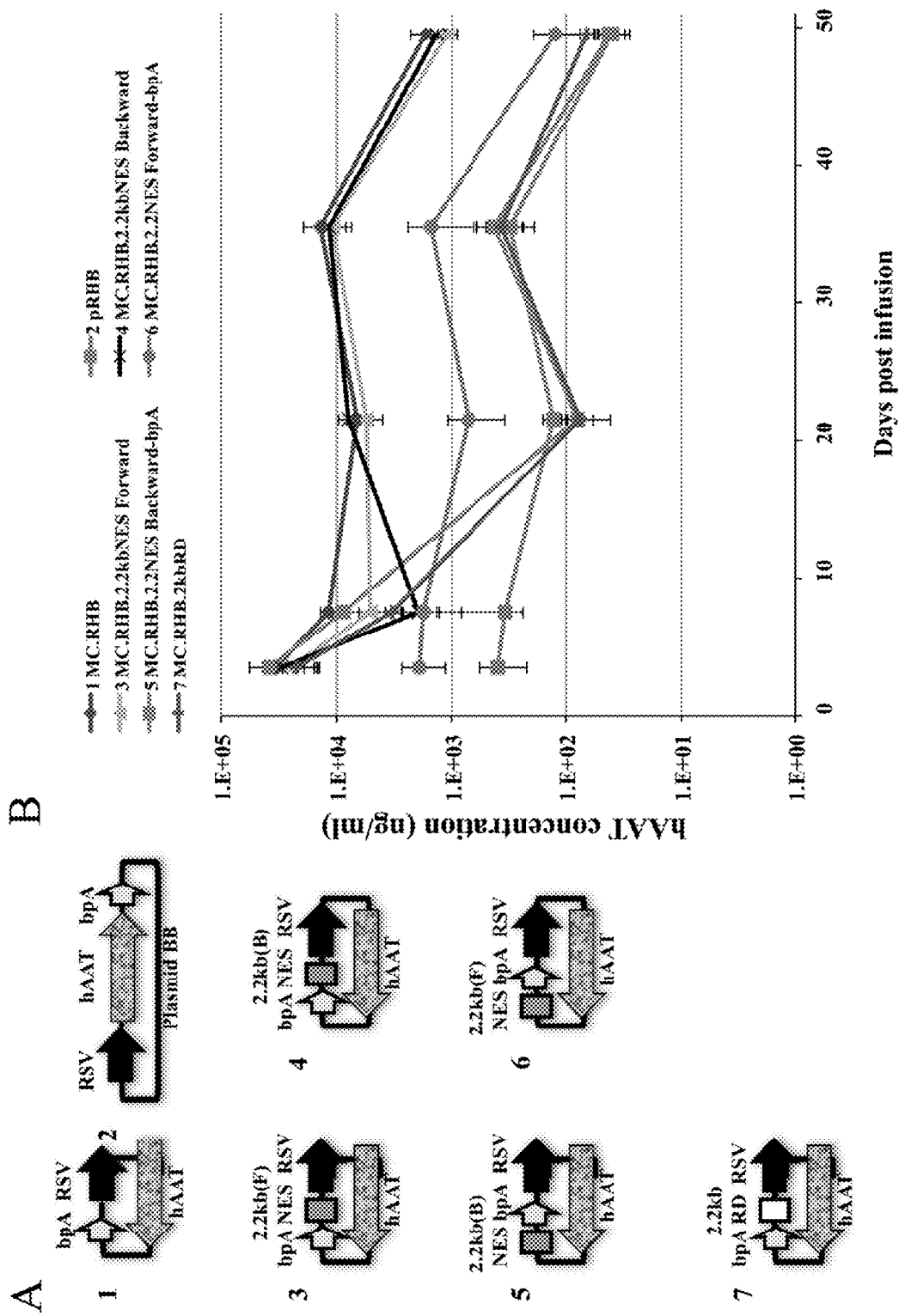
FIG. 11: RSV-hAAT expression constructs and transgene expression in mice. A) Schematic of hAAT expressing DNA constructs. 2.2 kb NES sequence in FIG. 2 was placed before or after bpA sequence as spacer. This spacer was placed in either forward (F) or backward (B) orientation. B) Serum hAAT levels at various time points after equimolar infusion of one of the plasmid vectors were infused. (n=5/group). Error bars represent the standard deviation. This figure indicates that 2.2 kb NES from FIG. 2 doesn't silence transgene expression when used as spacer and this effect is orientation independent.

As shown in FIG. 11, the 2.2 kb NES sequence in FIG. 10 was placed before or after bpA sequence as spacer. This spacer was placed in either forward (F) or backward (B) orientation. The NES sequence didn't silence transgene expression in vivo when used as spacers in minicircle DNA vector and this effect is orientation independent. When 2 kb random DNA (without poly T tracts) sequence was used as spacer, the transgene was quickly silenced in vivo (FIG. 11).

Figure 12:
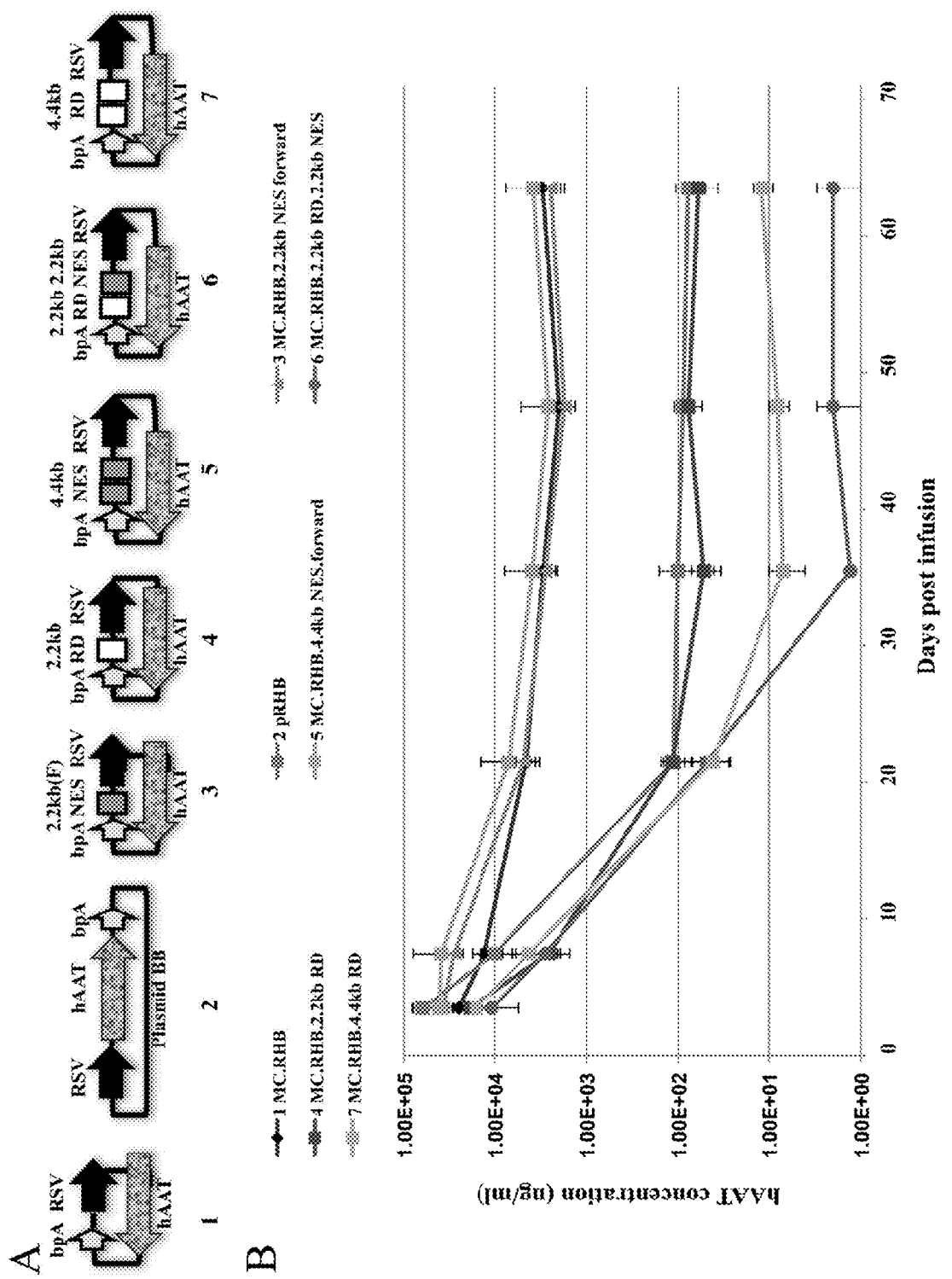
FIG. 12: RSV-hAAT expression constructs and transgene expression in mice. A) Schematic of hAAT expressing DNA constructs. One or two copies of 2.2 kb NES sequence in FIG. 2 or random DNA (RD) sequence was placed after bpA sequence as spacer. B) Serum hAAT levels at various time points after equimolar infusion of one of the plasmid vectors were infused. (n=5/group). Error bars represent the standard deviation. This figure indicates that while NES sequence doesn't silence transgene, the RD sequence at the same size is able to silence transgene. When NES and RD sequences are used together as spacer, the transgene is silenced.

To test whether an even longer NES (>2.2 kb) sequence can still retain transgene expression in vivo, we put two copies of NES sequences together to generate a 4.4 kb NES spacer. As a silencing control, two copies of 2 kb RD sequences were put together to generate 4 kb RD spacer. These constructs were tested for transgene expression in vivo, and the results were indicated in FIG. 12. As shown in FIG. 12, both 2.2 kb and 4.4 kb NES spacers were able to maintain transgene expression while 2 kb and 4 kb RD spacers silenced transgene expression in vivo.

Figure 13:
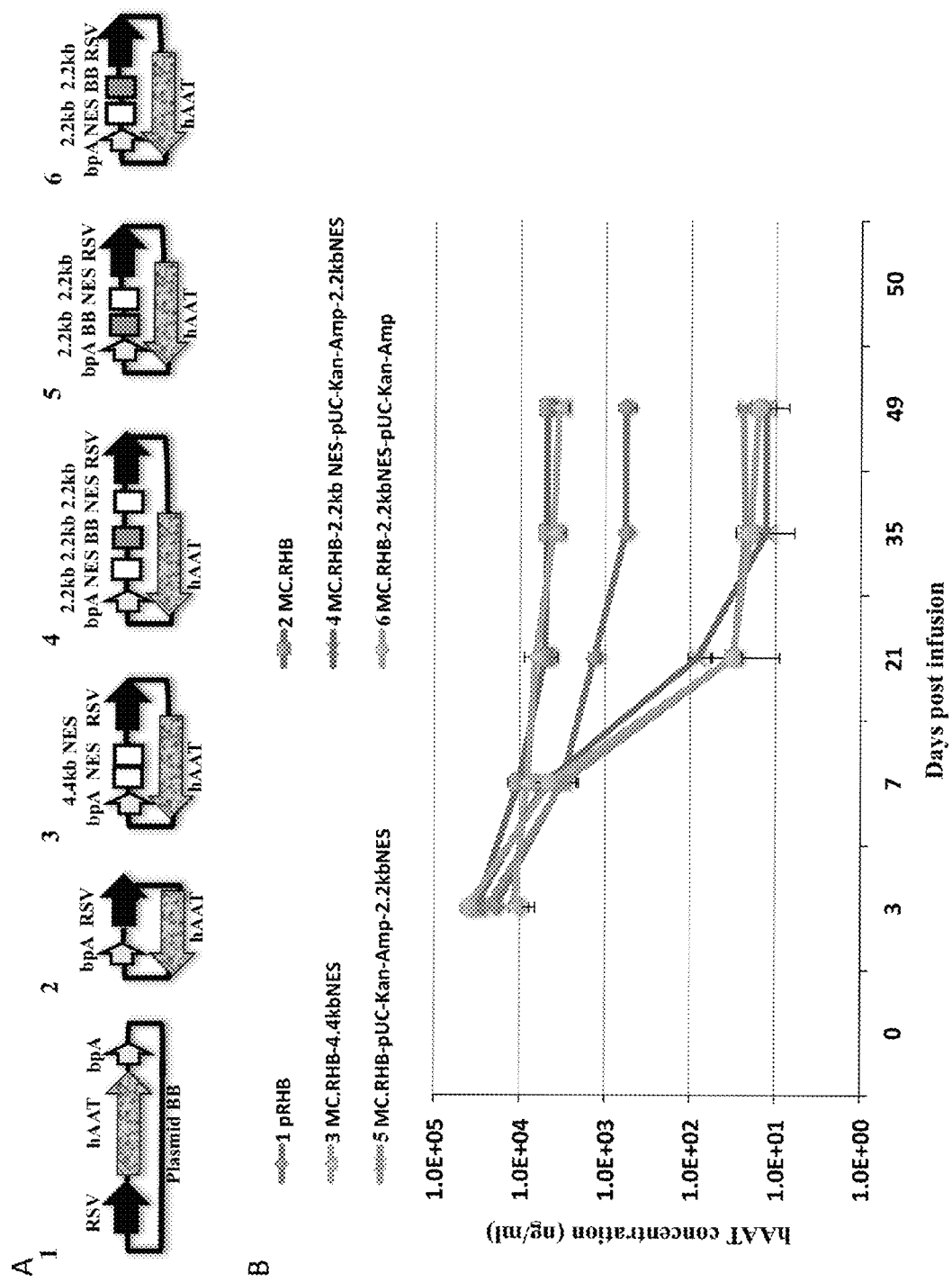
FIG. 13: RSV-hAAT expression constructs and transgene expression in mice. A) Schematic of hAAT expressing DNA constructs. NES sequence and/or bacterial backbone (BB) sequence were used as spacers in these constructs. B) Serum hAAT levels at various time points after equimolar infusion of one of the plasmid vectors were infused. (n=5/group). Error bars represent the standard deviation. This figure indicates that as long as there is a large BB sequence (2.2 kb in this figure), even in the presence of NES sequence on both sides of BB sequence, the transgene is silenced.
Figure 14:
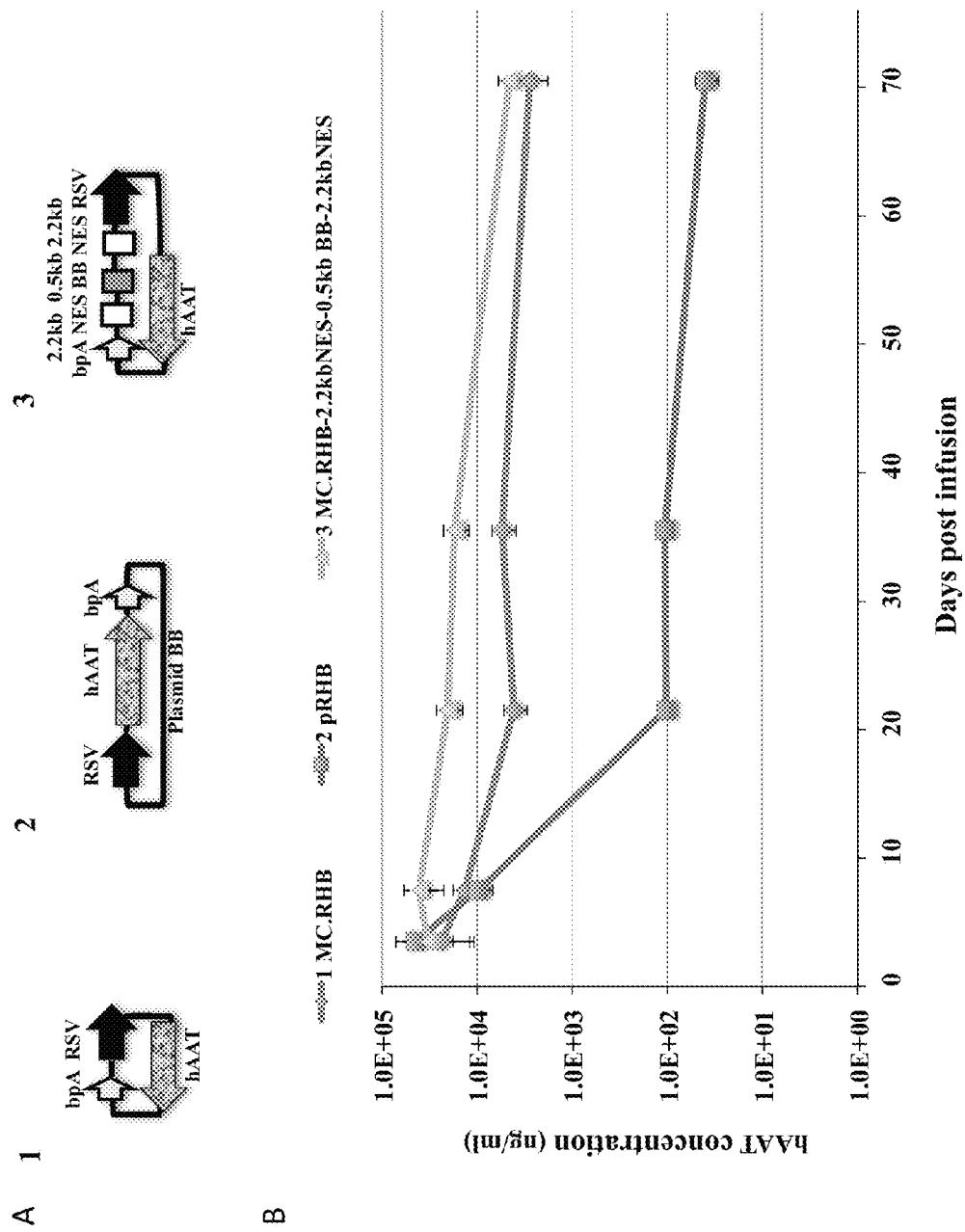
FIG. 14: RSV-hAAT expression constructs and transgene expression in mice. A) Schematic of hAAT expressing DNA constructs. NES sequence and/or bacterial backbone (BB) sequence were used as spacers in these constructs. The BB sequence contains 500 bp pUC sequence. B) Serum hAAT levels at various time points after equimolar infusion of one of the plasmid vectors were infused. (n=5/group). Error bars represent the standard deviation. This figure indicates that small BB sequence (0.5 kb in this figure) does not silence transgene when 2.2 kb NES sequence is used to flank the BB sequence.

Our previous studies indicate that noncoding, nonbacterial, and nongenic DNA sequences reaching 1 kb or more in length regardless of their origin can silence transgene expression in vivo. However 4.4 kb NES sequence doesn't silence transgene. To verify whether the NES sequence can rescue the silencing effect caused by RD and BB spacers, the different combinations of NES, RD and BB sequences were generated as spacers. As shown in FIGS. 12 and 13, silencing effects caused by 2.2 kb RD or 2.2 kb BB were not rescued by NES sequences in all tested combinations, even in the presence of NES sequence on both sides of BB sequence, the transgene is silenced. However as shown in FIG. 14, when small BB sequences are present, but are flanked by a larger NES sequence, there is no silencing. If we treat the NES sequence as part of the expression cassette that won't silence transgene, then these results are consistent with our previous findings that long (>1 kb) RD or BB sequences were able to silence transgene while short (500 bp) RD or BB sequences were not able to do so.

Figure 15:
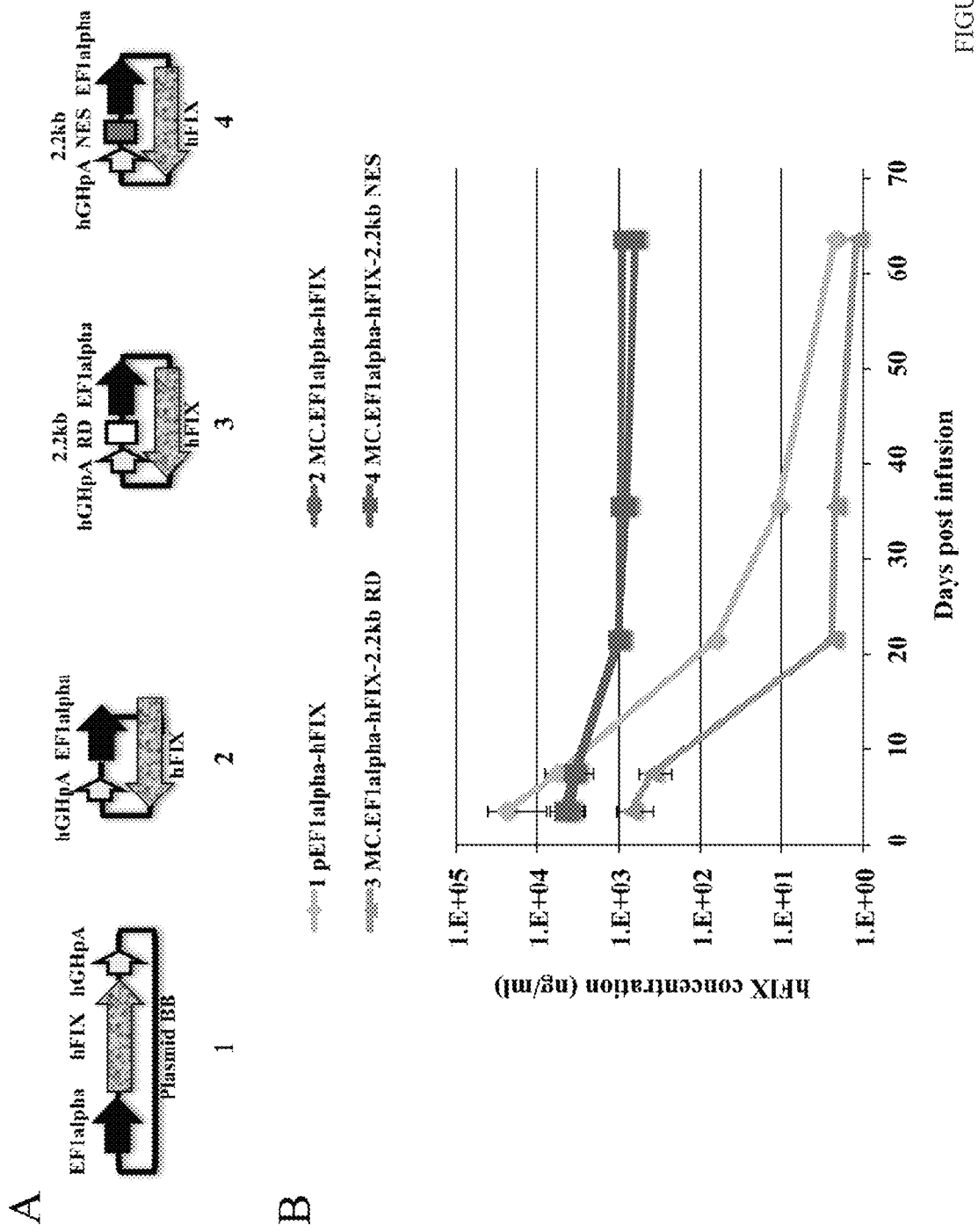
FIG. 15: EF1alpha-hFIX expression constructs and transgene expression in mice. A) Schematic of hFIX expressing DNA constructs. 2.2 kb NES sequence or 2.2 kb RD sequence was used as spacers in these constructs. B) The same molar amounts of DNA constructs shown in A were injected into mice (n=5/group) and the plasma hFIX levels were measured by ELISA at various time points. Error bars represent the standard deviation. This figure indicates that the effects of NES on transgene silencing are repeatable in another transgene expression system.

In order to verify that the non-silencing effect of NES sequence is not restricted to the tested RSV-hAAT-bpA expression cassette, the same 2.2 kb NES sequence was placed as spacer in EF1alpha-hFIX-hGHpA minicircle. As shown in FIG. 15, the presence of 2.2 kb NES as spacer did not silence transgene in vivo. However the presence of 2.2 kb RD as spacer silenced transgene expression. These indicate that the non-silencing effect of NES on transgene expression in vivo is a general effect.

A major limitation of nonviral plasmid vectors for gene therapy is the inability to achieve sustained therapeutic levels of transgene expression in vivo. The examples provided herein demonstrate that the plasmid silencing in vivo is not restricted to the covalent attachment of plasmid bacterial BB sequences. Rather noncoding, nonbacterial, and nongenic DNA sequences reaching 1 kb or more in length regardless of their origin can also silence transgene expression. However if the spacer sequence has a specific sequence arrangement (frequent A-tract or T-tract), such as NES sequence, the spacer will be able to retain the transgene expression in vivo without silencing.

The synthesized NES sequence in this study was generated by putting 20 bp of "T" tracts in every 60 bp of random DNA. The random DNA sequence came from the random DNA fragment tested as spacer in the previous experiment. While the same RD sequence silenced transgene when longer than 1 kb, the presence of the T-tracts reversed the results and made the RD containing T-tracts no longer able to silence transgene in vivo. In addition, this non-silencing effect of NES sequence is orientation independent. This indicates that the T-tracts or A-tracts play a crucial role in regulating transgene silencing in vivo. The T-tracts in NES sequence may function to exclude nucleosome binding at the spacer region and maintain the circular DNA vector at euchromatin formation.

What is claimed is:

1. A method of modifying a eukaryotic expression vector to generate a modified vector with reduced silencing of a transgene, wherein the eukaryotic expression vector comprises:
   (i) an expression cassette comprising, in a 5' to 3' order:
       (a) a promoter operably linked to a transgene or to a polylinker for insertion of a transgene, wherein the promoter is operable in a eukaryotic cell, (b) the transgene or said polylinker, and (c) a transcription termination sequence; and
   (ii) a gene silencing sequence that is at least 1 kilobase (kb) in length, positioned outside of the expression cassette, wherein the gene silencing sequence silences expression of the transgene,
   the method comprising: modifying the sequence of the gene silencing sequence by introducing AT tracts into the gene silencing sequence at intervals of from 60 to 250 nucleotides, thereby generating a modified vector with reduced transgene silencing.

2. The method of claim 1, wherein the vector is a plasmid, cosmid, viral or mini-circle vector.

3. The method of claim 1, wherein each AT tract is at least 15 nucleotides in length.

4. The method of claim 3, wherein each AT tract is not more than 35 nucleotides in length.

5. The method of claim 1, wherein one or more of said AT tracts is all A or all T nucleotides in one strand.

6. The method of claim 1, wherein one or more of said AT tracts is mixed A and T nucleotides on a single strand.

7. The method of claim 1, wherein the AT tracts are inserted into the gene silencing sequence at intervals of from 60 to 200 nucleotides.

8. The method of claim 1, wherein 10 to 20 AT tracts are introduced per 1 kilobase (kb) of gene silencing sequence.

9. The method of claim 1, wherein the gene silencing sequence comprises bacterial plasmid backbone sequence.

10. The method of claim 1, wherein the transgene comprises a sequence of interest selected from: a protein coding sequence, a sequence that encodes a non-translated RNA, a sequence that encodes a non-translated RNA that plays a role in RNA interference (RNAi), and a sequence that encodes an shRNA.

11. The method of claim 1, further comprising, after modifying the sequence, introducing said modified vector into an animal and verifying that the modified vector exhibits reduced transgene silencing.

12. A method for introducing an expression cassette comprising a transgene present in a modified vector into a cell of a mammal, said method comprising:
    modifying a eukaryotic expression vector by the method set forth in claim 1 to generate a modified vector; and introducing the modified vector into a cell of a mammal.

13. The method of claim 12, wherein the mammal is a mouse or a human.

14. The method of claim 12, wherein the mammal is a mouse.

15. A method of modifying a eukaryotic expression vector to generate a modified vector with reduced silencing of a transgene, wherein the eukaryotic expression vector comprises:
 (i) an expression cassette comprising, in a 5' to 3' order: (a) a promoter operably linked to a transgene or to a polylinker for insertion of a transgene, wherein the promoter is operable in a eukaryotic cell, (b) the transgene or said polylinker, and (c) a transcription termination sequence; and
 (ii) a gene silencing sequence that is at least 1 kilobase (kb) in length, positioned outside of the expression cassette, wherein the gene silencing sequence silences expression of the transgene,
 the method comprising: modifying the sequence of the gene silencing sequence by introducing AT tracts into the gene silencing sequence at intervals of from 60 to 250 nucleotides, thereby generating a modified vector with reduced transgene silencing,
 wherein the gene silencing sequence comprises a stretch of nucleotides (nt), positioned outside of the expression cassette and having a length of at least 80 nt but less than 1,000 nt, into which AT tracts are not inserted.

16. The method of claim 15, wherein the transgene comprises a sequence that encodes a protein or an shRNA, wherein the method comprises modifying the sequence of the gene silencing sequence by introducing AT tracts into the gene silencing sequence at intervals of from 60 to 250 nucleotides, wherein each AT tract is 18 to 30 nucleotides in length, wherein 10 to 20 AT tracts are introduced per 1 kilobase (kb) of gene silencing sequence, and wherein the modified vector reduces transgene silencing by at least 2-fold relative to the expression vector prior to said modifying.

17. The method of claim 15, wherein said stretch of nucleotides has a length of at least 250 nt but less than 1,000 nt.

18. The method of claim 15, wherein said stretch of nucleotides has a length of at least 500 nt but less than 1,000 nt.

* * * * *

SEQUENCE LISTING

<160> NUMBER OF SEQ ID NOS: 11

<210> SEQ ID NO 1
<211> LENGTH: 2718
<212> TYPE: DNA
<213> ORGANISM: Homo sapiens

<400> SEQUENCE: 1

| | | | | | |
|---|---|---|---|---|---|
| gaattcgttg | gaaacgggat | aatttcagct | gactaaacag | aagcagtctc | agaatcttct | 60 |
| ttgtgatgtt | tgcattcaaa | tccccgagtt | gaactttcct | ttcaaagttc | acgtttgaaa | 120 |
| cactctttt | gcaggatcta | caagtggata | tttggaccac | tctgtgtcct | tcgttcgaaa | 180 |
| cgggtatatc | ttcacatgcc | atctagacag | aagcatcctc | agaagcttct | ctgtgatgac | 240 |
| tgcattcaac | tcacggagtt | gaactctcct | tttgagagcg | cagttttgaa | actctctttc | 300 |
| tgtggcatct | gcaaggggac | atgtagacct | cttttgaagat | ttcgttggaa | acggaatcat | 360 |
| cttcacataa | aaactacaca | gatgcattct | caggaacttt | ttggtgatgt | ttgtattcaa | 420 |
| ctcccagagt | tgaactttcc | tttggaaaga | gcagctatga | aacactcttt | ttctagaatc | 480 |
| tgcaagtgga | cgtttggagg | gctttgtggt | tgtggtgga | aaaggaaata | tcttcaccta | 540 |
| aatactagat | agaagcattc | tcagaaactg | ctttgtgatg | attgcattca | cctcacagag | 600 |
| ttgaacattc | ctattgatag | agcagtttgg | aaacactctt | gttgtggaat | gtgcaagtgg | 660 |
| agatttggag | cgctttgagg | cctatggtag | taaagggaat | agcttcatag | aaaaactaga | 720 |
| cagaagcatt | ctcagaaaat | actttgtgat | gattgagttt | aactcacaga | gctgaacatt | 780 |
| cctttggatg | gagcaggttt | gagacactct | ttttgtacaa | tctacaagtg | gatatttgga | 840 |
| cctctctgag | gatttcgttg | gaaacgggat | aactgcacct | aactaaacgg | aagcattctc | 900 |
| agaaacttct | tggtgatgtt | tgcattcaaa | tcccagagtt | gaaccttcct | ttgatagttc | 960 |
| aggtttgaaa | cactctttt | gtaggatctg | caagtggata | tttggaccac | tctgtggcct | 1020 |
| tcgttcgaaa | cgggtatatc | ttcgcataaa | atctagacag | aagccttctc | agaaacttct | 1080 |
| ctgtgatgat | tgcattcaac | tcacagagtt | gaaccctcct | atggatagag | cagtgttgaa | 1140 |
| actctctttt | tgtggaatct | gcaagtggat | atgtggacct | ctccgaagat | gtctttggaa | 1200 |
| acggaatat | cttcacataa | aaactaaaca | gaagcattct | cagaaacttc | tctgtgatgt | 1260 |
| ttgtgttcaa | ctcccagagt | ttcacattgc | ttttcataga | gtagttctga | aacatgcttt | 1320 |
| tcgtagtgtc | tacaagtgga | catttggagc | gctttcaggc | ctgtggtgga | aaacgaatta | 1380 |
| tggtcacata | aaaactggag | agaagcattg | tcagaaactt | ctttgtgatg | attgcattca | 1440 |
| actcacagag | ttgaaggttc | cttttcaaag | agcagtttcc | aatcactctt | tgtgtggaat | 1500 |
| ctgcaagtgg | atatttggac | cttttttgaag | atttcgttgg | aaacgggaga | atcttcacag | 1560 |
| gaaagctaaa | cagaagcatt | ctcagaaact | tctttgtgat | gcttgcattc | aactcacaga | 1620 |
| gttgaacttt | cctttcgaga | gagaagcttt | gaaacactct | ttttccagaa | tctgcaagtg | 1680 |
| gacatttgga | gggctttgag | gcctgtggtg | gaaaaggaat | tatcttcccg | taaaagctag | 1740 |
| atagaagcat | tctcagaaac | tactttgtga | tgattgcatt | caagtcacag | agttgaacat | 1800 |
| tccctttgac | agagcagttt | ggaaactctc | tttgtgtaga | atctgcaagt | ggagatatgg | 1860 |
| accgctttag | gcctatggta | gtaaaggaaa | tagcttcata | taaaagctag | acagtagcat | 1920 |
| tcacagaaaa | ctcttggtga | cgactgagtt | taactcacag | agctgaacat | tcctttggat | 1980 |
| ggagcagttt | cgaaacacac | tatttgtaga | atgtgcaagt | ggatatttag | gcctctctga | 2040 |
| ggatttcgtt | ggaaacggga | taaaccgcac | agaactaaac | agaagcattc | tcagaaccctt | 2100 |

```
cttcgtgatg tttgcattca actcacagtg ttgaaccttt ctttgatagt tcaggtttga   2160
aacggtcttt ctgtagaaac tgcaagtaga tatttggacc gctctgagga tttcgttgga   2220
aacgggataa cccgcacaga actaaacaga agcattctca gaaccctctt cgtgatgttt   2280
gcattcaact cacagtgctg aacctttctt tgatagttca gctttgaaac actcttttg    2340 tagaaactgc aagtggatat ttggtcctct ctgagcattt cgttggaaac gggataaact   2400
gcacagaact aaacagaagc actctcagaa ccttcttcgt gatgtctgca ttcaactcac   2460
agtgtggaac ctttctttga tagttcaggt ttgaaacact ctttttgtag aaactgcaag   2520
gggatcattg cactctttga ggagtaccgt agtaaaggaa ataacttcct ataaaagaa    2580 gacagaagct ttctcagaaa attctttggg atgattgagt tgaactcaca gagctgagca   2640
ttccttgcga tgtagcagtt tagaaacaca cttcctgcag aatctgcaat tgcatatttg    2700
gacctctttg aggaattc                                                2718
```

<210> SEQ ID NO 2
<211> LENGTH: 2191
<212> TYPE: DNA
<213> ORGANISM: Artificial Sequence
<220> FEATURE:
<223> OTHER INFORMATION: Synthetic oligonucleotide

<400> SEQUENCE: 2

```
gctagcgtcg actccggcga acgactatat tatcagctta cgatccccg cggagccttc      60 cgattctttc cggctcttac tacctcgcct ccgtaggccc gcggctagtt tctatcctcc    120
aacgtaaatc ccgagccgag ctgtgactcc cgaaggccgg tctcctgtca cgtatccggt    180
ggctgtgcgc gtacaccacc agccgggtcg gcgagtctat tgcatagttt tgcgagcgaa    240
tatgctttgc ccttcacgg tgctggtatc atgccgcggc gctccatcca cttctctccc     300
ttgcttatcg cgcctaccat ccctatacag acgtcggagt tcgtttctcg aaactgtctt    360
tccgacagcc ggattccacc gggcgcagcg ttcctctcga gcgcggtag cacgtcttac     420 agacagttct tccggcttcg agttgaacat tctgcatctt aaccttcatt tattccattc    480
tcgcgagccg ccgatctact gagacagcga gcgttccatc gttcttttct ctttctttcg    540
cggcgagacc caccttccgg gcgccgcgcg gcgggtttac ttactactcg cggagttaag    600
cggccctgcc gggcgcgggct ccaccgcgcc tcgacgtagg gtgtcttccg gggggggttta   660 catactattc cagcgttctt gttattttcc cgcggcggct ttagactatc ggctgttcgg    720
ccttcttctt cccttcgatc gccaggcagg agtctcaagt tctcgcgagt atctgctttg    780 tttttattc aaatacctcc gactagccaa atctttctcc gttgggtccc atcttatatt     840
ccagctcaga gtccctcgca tcgcctgcgc tccctccgca gttttccttg cgggattcta    900
ctcgataacc tgtcttgctt atccggaatc cgtagtacgt ccgcgcggta ctcgagcgta    960
tctgcccatc ctactatatc tttctgcgtt ctagcgtcga ccccgcgcct catttagaca   1020
gggcctggag ttagtcctgg ctccagctgg ccacgatttt atatagcccc tctcctattc   1080
tggctccccg ggaatgacga aagcttgaat tcttctattc cgccgcgggg atgaggccgg   1140
tggcgtgatt catgcggact atgccccgcg gtgccgggtc ggcgcgtcgc gattttttct   1200
ccgcgggcca ggcaggtggc tccctaaagt tgctccaggc gcggtcgcca atgggagaac   1260
tctaatcgct cccgcttctt ctacgattcg ctaagacacc tgcgcaaggg cttaatcttc   1320
ccagctgttt ctaggcggtt ttccccccaga cccgcgcggg cgtcatgtat gctcgacggg   1380
ttccttcccg cgtgatgttt ccacgcgtg atttctgggg ctgaggccac gctctactac   1440
```

| | |
|---|---|
| accagtcaat tatgagttac tccccactca actttccatg cggcttttac gcccgcggct | 1500 |
| ataagcgtca agttctatca ttttatagcg gactctactg cggtaaactt cgagaccgga | 1560 |
| tcctggtccg gacgaatgtc ttatttatct ctttacaact atcgcccggg ttgctttgta | 1620 |
| ctccagccat ttacacgtta tctagcgtcg accggggcag ctgtaggtcc ggatacataa | 1680 |
| cagggaaagg tcttatttct aatatcggcc atttatcgta cttagttgtc tcttctacgc | 1740 |
| gcacaactat taaatgttga atttgtacgg cggtcgccgg cgggacccgt gggaaagagt | 1800 |
| tcgttccctc gtagctctcc tcaataacta atcctggtaa tatgcaccga gcccacacgg | 1860 |
| gcttatcgcc cgaggatccg tttaatttgt aatagaattg cgcgcgtggt gaatatctcg | 1920 |
| gtttacccag gttggcagtc ctttattccg ggctcggcgg tggagtaagc ccggcttgtt | 1980 |
| ttccccttc ttttttttcta ttttgtatct ccctcgcggc taaatccatc gagaagttat | 2040 |
| attatccgca cggcgcgagg tcgctcgtcc atgcacggca tagttcagtt accggcgcag | 2100 |
| tctttattgt aattacgccg agggtgcacg agccctctt cggacgttgc aggtaaccag | 2160 |
| cctagcctgc tagtaccatt aaccgagcag t | 2191 |

<210> SEQ ID NO 3
<211> LENGTH: 2180
<212> TYPE: DNA
<213> ORGANISM: Artificial sequence
<220> FEATURE:
<223> OTHER INFORMATION: Synthetic oligonucleotide

<400> SEQUENCE: 3

| | |
|---|---|
| tttttttttt tttttttttt gtcgactccg gcgaacgact atattatcag cttacgatcc | 60 |
| cccgcggagc cttccgattc tttttttttt tttttttttt ccggctctta ctacctcgcc | 120 |
| tccgtaggcc cgcggctagt ttctatcctc aacgtaaat tttttttttt tttttttttt | 180 |
| cccgagccga gctgtgactc ccgaaggccg gtctcctgtc acgtatccgg tggctgtgcg | 240 |
| tttttttttt tttttttttt cgtacaccac cagcccgggtc ggcgagtcta ttgcatagtt | 300 |
| ttgcgagcga atatgctttg tttttttttt tttttttttt ccctttcacg gtgctggtat | 360 |
| catgccgcgg cgctccatcc acttctctcc cttgcttatc tttttttttt tttttttttt | 420 |
| gcgcctacca tccctataca gacgtcggag ttcgtttctc gaaactgtct ttccgacagc | 480 |
| tttttttttt tttttttttt cggattccac cgggcgcagc gttcctctcg agcggcggta | 540 |
| gcacgtctta cagacagttc tttttttttt tttttttttt ccggcttcga gttgaacatt | 600 |
| ctgcatctta accttcattt attccattct cgcgagccgc tttttttttt tttttttttt | 660 |
| cgatctactg agacagcgag cgttccatcg ttctttcttc tttctttcgc ggcgagaccc | 720 |
| tttttttttt tttttttttt accttccggg cgccgcgcgg cgggtttact tactactcgc | 780 |
| ggagttaagc ggccctgccg tttttttttt tttttttttt ggcgcggctc caccgcgcct | 840 |
| cgacgtaggg tgtcttccgg gggggtttac atactattcc tttttttttt tttttttttt | 900 |
| agcgttcttg ttattttccc gcggcggctt tagactatcg gctgttcggc cttcttcttc | 960 |
| tttttttttt tttttttttt ccttcgatcg ccaggcagga gtctcaagtt ctcgcgagta | 1020 |
| tctgctttgt ttttttattca tttttttttt tttttttttt aataccctccg actagccaaa | 1080 |
| tctttctccg ttgggtccca tcttatattc cagctcagag tttttttttt tttttttttt | 1140 |
| ccctcgcatc gcctgcgctc cctccgcagt tttccttgcg ggattctact cgataacctg | 1200 |
| tttttttttt tttttttttt cttgcttatc cggaatccgt agtacgtccg cgcggtactc | 1260 |
| gagcgtatct gcccatccta tttttttttt tttttttttt ctatatcttt ctgcgttcta | 1320 |

```
gcgtcgaccc cgcgcctcat ttagacaggg cctggagtta tttttttttt tttttttttt    1380
gtcctggctc cagctggcca cgattttata tagcccctct cctattctgg ctccccggga    1440
tttttttttt tttttttttt atgacgaaag cttgaattct tctattcccg ccgcgggatg    1500
aggccggtgg cgtgattcat tttttttttt tttttttttt gcggactatg ccccgcggtg    1560
ccgggtcggc gcgtcgcgat ttttctccg cgggccaggc tttttttttt tttttttttt    1620
ggtggctccc taaagttgct ccaggcgcgg tcgccaatgg gagaactcta atcgctcccg    1680
tttttttttt tttttttttt cttcttctac gattcgctaa gacacctgcg caagggctta    1740
atcttcccag ctgtttctag tttttttttt tttttttttt gcggttttcc cccagacccg    1800
cgcgggcgtc atgtatgctc gacgggttcc ttcccgcgtg tttttttttt tttttttttt    1860
atgttttcca cgcgtgattt tctgggctga ggccacgctc tactacacca gtcaattatg    1920
tttttttttt tttttttttt agttactccc cactcaactt tccatgcggc ttttacgccc    1980
gcggctataa gcgtcaagtt tttttttttt tttttttttt ctatcatttt atagcggact    2040
atacgcctgt aaacttcgag accggatcct ggtccgaaag tttttttttt tttttttttt    2100
aaagattatt tatctcttta cactatcgcc ccggttgctt tgtactccag ccattaaaca    2160
tttttttttt tttttttttt                                                2180

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
acgcgtccaa ttgcctttct                                                  20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ctcgaggttg aaggtctcaa                                                  20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
acattgccct tctggaactg                                                  20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gctgatctcc ctttgtggaa                                                  20
```

```
<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
aaggcaaatg ggagagacct                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
tacccagctg gacagcttct                                               20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ttgctgacag gatgcagaag                                               20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tgatccacat ctgctggaag                                               20
```